United States Patent
Joo et al.

(10) Patent No.: US 12,065,694 B2
(45) Date of Patent: *Aug. 20, 2024

(54) KITS FOR SINGLE-STEP ANALYTE DETECTION WITH PROCESS CONTROL

(71) Applicant: GEN-PROBE INCORPORATED, San Diego, CA (US)

(72) Inventors: Sunghae A. Joo, San Diego, CA (US); Janel M. Dockter, Oceanside, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 212 days.

This patent is subject to a terminal disclaimer.

(21) Appl. No.: 17/388,410

(22) Filed: Jul. 29, 2021

(65) Prior Publication Data

US 2021/0355528 A1     Nov. 18, 2021

Related U.S. Application Data

(63) Continuation of application No. 16/657,749, filed on Oct. 18, 2019, now Pat. No. 11,104,935, which is a continuation of application No. 15/729,128, filed on Oct. 10, 2017, now Pat. No. 10,487,353, which is a (Continued)

(51) Int. Cl.
　　*C12Q 1/6816*　　(2018.01)
　　*C12Q 1/6844*　　(2018.01)
(52) U.S. Cl.
　　CPC ......... *C12Q 1/6816* (2013.01); *C12Q 1/6844* (2013.01)

(58) Field of Classification Search
　　CPC .......... C12Q 1/6816; C12Q 1/6844; C12Q 2545/114; C12Q 2545/101; C12Q 2537/165
　　See application file for complete search history.

(56) References Cited

U.S. PATENT DOCUMENTS

| | | |
|---|---|---|
| 4,581,333 A | 4/1986 | Kourilsky et al. |
| 4,683,195 A | 7/1987 | Mullis et al. |
| 4,683,202 A | 7/1987 | Mullis |

(Continued)

FOREIGN PATENT DOCUMENTS

| | | |
|---|---|---|
| EP | 0 684 315 A1 | 11/1995 |
| EP | 0 747 706 A1 | 11/1996 |

(Continued)

OTHER PUBLICATIONS

Arnold et al., "Assay Formats Involving Acridinium-Ester-Labeled DNA Probes," Clin. Chem., 1989, 35 (8):1588-1594, American Assoc. for Clinical Chemistry, USA.

(Continued)

*Primary Examiner* — Joseph G. Dauner
(74) *Attorney, Agent, or Firm* — Michael J. Gilly

(57) ABSTRACT

Kits for detecting analyte polynucleotides and an internal control in a sample. Included in the kit are an internal control polynucleotide and amplification reagents to co-amplify a first analyte polynucleotide and the internal control. Also included are first and second hybridization probes, each having a label indistinguishable from the other. The probes are respectively capable of hybridizing with a first analyte amplicon and an internal control amplicon. The first and second labels are indistinguishable homogeneous labels.

22 Claims, 2 Drawing Sheets

Related U.S. Application Data continuation of application No. 13/173,558, filed on Jun. 30, 2011, now Pat. No. 9,822,397.

(60) Provisional application No. 61/360,296, filed on Jun. 30, 2010.

(56) References Cited

U.S. PATENT DOCUMENTS

| | | | |
|---|---|---|---|
| 4,800,159 A | 1/1989 | Mullis et al. | |
| 4,968,603 A | 11/1990 | Slamon et al. | |
| 5,130,238 A | 7/1992 | Malek et al. | |
| 5,270,184 A | 12/1993 | Walker et al. | |
| 5,283,174 A | 2/1994 | Arnold, Jr. et al. | |
| 5,310,652 A | 5/1994 | Gelfand et al. | |
| 5,322,770 A | 6/1994 | Gelfand | |
| 5,378,825 A | 1/1995 | Cook et al. | |
| 5,399,491 A | 5/1995 | Kacian et al. | |
| 5,455,166 A | 10/1995 | Walker | |
| 5,480,784 A | 1/1996 | Kacian et al. | |
| 5,539,082 A | 7/1996 | Nielsen et al. | |
| 5,547,842 A | 8/1996 | Hogan et al. | |
| 5,585,481 A | 12/1996 | Arnold, Jr. et al. | |
| 5,591,578 A | 1/1997 | Meade et al. | |
| 5,639,604 A | 6/1997 | Arnold, Jr. et al. | |
| 5,656,207 A | 8/1997 | Woodhead et al. | |
| 5,658,737 A | 8/1997 | Nelson et al. | |
| 5,770,369 A | 6/1998 | Meade et al. | |
| 5,811,269 A * | 9/1998 | Nadeau | C12Q 1/689 536/24.32 |
| 5,854,033 A | 12/1998 | Lizardi | |
| 5,925,517 A | 7/1999 | Tyagi et al. | |
| 6,015,674 A | 1/2000 | Woudenberg et al. | |
| 6,083,482 A | 7/2000 | Wang | |
| 6,130,038 A | 10/2000 | Becker et al. | |
| 6,225,067 B1 | 5/2001 | Rogers | |
| 6,268,490 B1 | 7/2001 | Imanishi et al. | |
| 6,300,068 B1 | 10/2001 | Burg et al. | |
| 6,312,929 B1 | 11/2001 | McMillan | |
| 6,361,945 B1 | 3/2002 | Becker et al. | |
| 6,410,278 B1 | 6/2002 | Notomi et al. | |
| 6,586,234 B1 | 7/2003 | Burg et al. | |
| 6,670,461 B1 | 12/2003 | Wengel et al. | |
| 6,949,367 B1 | 9/2005 | Dempcy et al. | |
| 7,510,837 B2 | 3/2009 | Gao et al. | |
| 9,822,397 B2 | 11/2017 | Joo et al. | |
| 10,487,353 B2 | 11/2019 | Joo et al. | |
| 11,104,935 B2 | 8/2021 | Joo et al. | |
| 2002/0119464 A1 | 8/2002 | McMillan | |
| 2003/0064368 A1 | 4/2003 | Sakai et al. | |
| 2003/0105320 A1 | 6/2003 | Becker et al. | |
| 2003/0108921 A1 | 6/2003 | Jucker et al. | |
| 2004/0029111 A1 | 2/2004 | Linnen et al. | |
| 2004/0058378 A1 | 3/2004 | Kong et al. | |
| 2004/0063147 A1 | 4/2004 | Natrajan et al. | |
| 2006/0046265 A1 | 3/2006 | Becker et al. | |
| 2006/0188912 A1 * | 8/2006 | Gao | C12N 15/1006 435/6.12 |
| 2006/0292571 A1 | 12/2006 | Babiel et al. | |
| 2012/0003646 A1 | 1/2012 | Joo et al. | |

FOREIGN PATENT DOCUMENTS

| | | |
|---|---|---|
| EP | 0875584 A2 | 11/1998 |
| EP | 1045036 A2 | 10/2000 |
| WO | 93/13121 A1 | 7/1993 |
| WO | 95/32305 A1 | 11/1995 |
| WO | 98/57158 A1 | 12/1998 |
| WO | 2006034215 A1 | 3/2006 |
| WO | 2008/007242 A2 | 1/2008 |
| WO | 2010007355 A1 | 1/2010 |

OTHER PUBLICATIONS

Guatelli et al., "Isothermal, in vitro amplification of nucleic acids by a multienzyme reaction modeled after retroviral replication," Proc. Natl. Acad. Sci. USA, 1990, 87:1874-1878, National Academy of Sciences, Washington D.C., USA.

Giachetti et al., "Highly Sensitive Multiplex Assay for Detection of Human Immunodeficiency Virus Type 1 and Hepatitis C Virus RNA," J. Clin. Microbiol., 2002, 40(7):2408-2419, American Society for Microbiology, Washington D.C., USA.

Hoorfar et al., "Practical considerations in design of internal amplification controls for diagnostic PCR assays," J Clin Microbiol. May 2004;42(5):1863-8, American Society for Microbiology, Washington D.C., USA.

Joo et al., Abstract only, "Preliminary Evaluation of the APTIMA-AEHPV 16 18/45 Genotype Assay for the Detection of Human Papillomavirus Types 16, 18, and 45 in Liquid Pap Specimen," 26th International Papillomavirus Conference & Clinical and Public Health Workshops, Jul. 3, 2010, Montreal, Canada.

Joo et al., Poster, "Preliminary Evaluation of the APTIMA® HPV 16 18/45 Genotype Assay for the Detection of Human Papillomavirus Types 16, 18 and 45 in Liquid Pap Specimens," 26th International Papillomavirus Conference & Clinical and Public Health Workshops, Jul. 5, 2010. Montreal, Canada.

Kiviniemi et al., "A homogeneous high-throughput genotyping method based on competitive hybridization," Clin. BioChem., 2003, 36:633-640, Elsevier, USA.

Kwoh et al., "Transcription-based amplification system and detection of amplified human immunodeficiency virus type 1 with a bead-based sandwich hybridization format," Proc. Natl. Acad. Sci. USA, 1989, 86:1173-1177, National Academy of Sciences, Washington D.C., USA.

McCormick et al., "Evaluation of a new molecular assay for detection of human immunodeficiency virus type 1 RNA, hepatitis C virus RNA, and hepatitis B virus DNA," J. Clin. Virol., 2006, 36:166-176, Elsevier Science, Amsterdam, Netherlands.

Nelson et al., "Simultaneous Detection of Multiple Nucleic Acid Targets in a Homogeneous Format," Biochemistry, 1996, 35:8429-8438, American Chemical Society, Washington D.C., USA.

Sanchez et al., "Linear-after-the-exponential (LATE)-PCR: an advanced method of asymmetric PCR and its uses in quantitative real-time analysis," Proc Natl Acad Sci US A. Feb. 17, 2004;101(7):1933-8. Epub Feb. 9, 2004. Brandeis University, Massachusetts, USA.

Sjöroos et al., "Solid-Phase PCR with Hybridization and Time-resolved Fluorometry for Detection of HLA-B27," Clin. Chem., 2001, 43(3):498-504, American Assoc. for Clinical Chemistry, USA.

Vester et al., "LNA (Locked Nucleic Acid): High-Affinity Targeting of Complementary RNA and DNA," Biochemistry, 2004, 43(42):13233-13241, American Chemical Society, Washington D.C., USA.

Walker et al., "Strand displacement amplification—an isothermal, in vitro DNA amplification technique," Nucleic Acids Research, 1992, 20(7):1691-1696, Oxford University Press, Oxford, United Kingdom.

Walker et al., "Isothermal in vitro amplification of DNA by a restriction enzyme/ DNA polymerase system," Proc. Natl. Acad. Sci. USA, 1992, 89:392-396, National Academy of Sciences, Washington D.C., USA.

PCT Search Report and Written Opinion, PCT Application No. PCT/US11/42549, Nov. 30, 2011.

IPA Office Action, Australian Patent Application No. 2011272868, Oct. 1, 2014.

CIPO Office Action, Canadian Patent Application No. 2,802,741, Jun. 29, 2017.

CIPO Notice of Allowance, Canadian Patent Application No. 2,802,741, Dec. 23, 2019.

SIPO Office Action, Chinese Patent Application No. 201180032676.3, Dec. 4, 2013.

SIPO Office Action, Chinese Patent Application No. 201180032676.3, Aug. 15, 2014.

EPO Communication under Rule 71(3) EPC, European Patent Application No. 11738522.9, Dec. 14, 2016.

EPO Decision to grant a European patent pursuant to Article 97(1) EPC, European Patent Application No. 11738522.9, Apr. 21, 2017.

(56) References Cited

OTHER PUBLICATIONS

EPO Communication pursuant to Article 94(3), European Patent Application No. 11 738 522.9, Dec. 7, 2015.
EPO Office Action, European Patent Application No. 11738522.9, Mar. 27, 2014.
USPTO, Non-Final Rejection, U.S. Appl. No. 13/173,558, Mar. 28, 2013.
USPTO, Non-Final Rejection, U.S. Appl. No. 13/173,558, Oct. 3, 2013.
USPTO, Final Rejection, U.S. Appl. No. 13/173,558, Feb. 13, 2014.
USPTO, Advisory Action, U.S. Appl. No. 13/173,558, Apr. 24, 2014.
USPTO, Advisory Action, U.S. Appl. No. 13/173,558, May 8, 2014.
USPTO, Non-Final Rejection, U.S. Appl. No. 13/173,558, Sep. 12, 2014.
USPTO, Final Rejection, U.S. Appl. No. 13/173,558, Apr. 2, 2015.
USPTO, Advisory Action, U.S. Appl. No. 13/173,558, Jul. 23, 2015.
USPTO, Final Rejection, U.S. Appl. No. 13/173,558, Mar. 10, 2016.
USPTO, Final Office Action, U.S. Appl. No. 13/173,558, Nov. 1, 2016.
USPTO, Pre-Brief Appeal Conference Decision, U.S. Appl. No. 13/173,558, Jun. 22, 2017.
USPTO, Notice of Allowance, U.S. Appl. No. 13/173,558, Jul. 11, 2017.
USPTO, Non-Final Rejection, U.S. Appl. No. 15/729,128, Jan. 22, 2019.
USPTO, Notice of Allowance, U.S. Appl. No. 15/729,128, Jul. 25, 2019.
USPTO, Non-Final Rejection, U.S. Appl. No. 16/657,749, Nov. 23, 2020.
USPTO, Notice of Allowance, U.S. Appl. No. 16/657,749, May 7, 2021.

* cited by examiner

KITS FOR SINGLE-STEP ANALYTE DETECTION WITH PROCESS CONTROL

RELATED APPLICATIONS

This application is a continuation of U.S. application Ser. No. 16/657,749, filed Oct. 18, 2019, now U.S. Pat. No. 11,104,935, which is a continuation of U.S. application Ser. No. 15/729,128, filed Oct. 10, 2017, now U.S. Pat. No. 10,487,353, which is a continuation of U.S. application Ser. No. 13/173,558, filed Jun. 30, 2011, now U.S. Pat. No. 9,822,397, which claims the benefit of U.S. Provisional Application No. 61/360,296, filed Jun. 30, 2010. The disclosures of these prior applications are hereby incorporated by reference in their entireties.

TECHNICAL FIELD

The present invention relates to the sub-field of biotechnology that concerns diagnostic assays. More particularly, the invention relates to analyte detection in an assay that includes an internal control, where the analyte and internal control are detected using different probes. In a highly preferred embodiment, nucleic acid analytes are detected in a single mixture using different hybridization probes that harbor identical detectable labels.

BACKGROUND

Modern assays for detecting the presence of an analyte (e.g., a nucleic acid, protein, lipid, carbohydrate, and the like) rely on the use of a positive control to verify process reliability. For example, an assay may seek to detect a target nucleic acid using nucleic acid amplification followed by probe hybridization and detection. The sample undergoing amplification can include an internal control (hereafter, "IC") nucleic acid that co-amplifies with the analyte nucleic acid. Amplification products advantageously can have non-identical sequences that can be detected using different hybridization probes. Detection of the IC amplification product verifies integrity of the amplification and detection components of the assay procedure. That information is useful when there is a failure to detect analyte amplification products. Detection of the IC signal, in such a case, validates the analyte-negative result. Hybridization probes specific for analyte amplicons, and for IC amplicons are conventionally distinguished either by the labels they harbor, or by spatial separation.

Probe-based assays, including protein and nucleic acid assays, that include an internal process control commonly make one of the following distinctions with respect to detection of IC and analyte: (1) IC is detected separate from analyte; and (2) analyte is detected separate from the combination of analyte plus IC. U.S. Pat. No. 6,586,234 illustrates both of these possibilities using two-read systems for detection of IC and analyte nucleic acids. When analyte nucleic acid is detected independent of the combination of IC plus analyte, the latter hybridization signal can be evaluated for samples yielding analyte hybridization signals that fall below a threshold cutoff required for positive scoring. For example, a signal below the threshold cutoff for analyte detection may alternatively indicate absence of analyte, or malfunction in the assay. If a signal is detected in a second read that represents the combination of IC plus analyte, that result is interpreted as validating the analyte-negative result. In other words, detection of an adequate signal for IC plus analyte indicates that IC must have been detected, and so can validate an analyte-negative result. It should be apparent that success of such a system depends on the ability to separate the analyte hybridization signal from the combination of hybridization signals representing IC and analyte.

One difficulty encountered in the field of analyte detection concerns the number of different labels required for analysis of multiplex reactions when detection is carried out without spatial separation between different probes (e.g., the different probes being in fluid communication, and free in solution rather than immobilized). This may be understood in the context of an assay that co-amplifies an IC nucleic acid and two different target nucleic acids. With the IC probe harboring one label, a collection of probes for detecting the remaining two targets can be labeled with a second label. A positive detection signal for the second label indicates that one of the two analytes is present, but fails to differentiate one from the other. As the number of analytes climbs, the amount of re-testing needed to resolve the reactive species increases similarly. Stated differently, the burden of re-testing to identify the reactive species in positively scoring multiplex assays is a disadvantage, especially when the fraction of positive samples becomes significant.

The present invention addresses the need for simplified analyte identification systems.

SUMMARY

In one aspect the invention relates to an apparatus for determining, with process control, the presence or absence of a first analyte in a sample that includes an internal control. Generally speaking, the invented apparatus includes: (a) a holder configured to contain the sample; (b) an optical detection mechanism arranged to receive optical signals from the sample when contained in the holder; and (c) a processor (e.g., a computer) in communication with the optical detection mechanism, the processor being programmed to perform the step of determining which of a number of situations applies. In accordance with the invention, in addition to the internal control the sample further includes: an internal control probe that generates an internal control signal after contacting the internal control; a first analyte probe that generates a first analyte signal after contacting the first analyte, if present in the sample; and optionally a second analyte probe that generates a second analyte signal after contacting a second analyte, if present in the sample. Further in accordance with the invention, the optical detection mechanism is configured to measure a combined signal generated by the internal control probe and the analyte probe without distinguishing the internal control signal from the analyte signal. The optical detection mechanism is optionally configured to measure the second analyte signal generated by the second analyte probe. Still further in accordance with the invention, the processor is programmed to determine which of the following situations applies: (i) the sample does not include the first analyte if the magnitude of the combined signal is less than a first analyte cutoff value and either (1) the magnitude of the combined signal is greater than or equal to a validity cutoff value, or (2) the second analyte probe is included in the sample, the optical detection mechanism is configured to measure the second analyte signal, and the magnitude of the second analyte signal is greater than or equal to a second analyte cutoff value, thereby establishing that the sample includes the second analyte; (ii) the sample includes the first analyte if the magnitude of the combined signal is greater than or equal to the first analyte cutoff value, and (iii) it cannot be determined whether or not the sample includes the first analyte if the magnitude of the combined signal is less than the first analyte cutoff value and less than the validity cutoff value, and, if the second analyte probe is included in the reaction mixture, and the optical detection mechanism is configured to measure the second analyte signal, the second analyte signal is less than the second analyte cutoff value. Generally, the first analyte cutoff value is a signal amount greater than the validity cutoff value, and the detectable maximum of the internal control signal cannot exceed the first analyte cutoff value.

In accordance with a first highly preferred embodiment of the generally described apparatus for determining, with process control, the presence or absence of a first analyte in a sample that includes an internal control, the optical detection mechanism is configured to measure the second analyte signal generated by the second analyte probe. When this is the case, it is preferred that the holder does not substantially change temperature during operation of the optical detection mechanism to measure the combined signal; the first analyte, the second analyte, and the internal control each include nucleic acid; and the optical detection mechanism does not measure the first analyte signal without also measuring the internal control signal. Alternatively, it is preferred that the optical detection mechanism does not measure the first analyte signal without also measuring the internal control signal; and that the apparatus further includes an output device that produces a tangible record (e.g., a printed record, or an electronic record stored on computer-readable media) of the determining step performed by the processor. More preferably, the holder does not substantially change temperature during operation of the optical detection mechanism to measure the combined signal; the first analyte, the second analyte, and the internal control each include nucleic acid; and the optical detection mechanism does not measure the first analyte signal without also measuring the internal control signal. When this is the case, it is preferred that the sample maintains substantially constant temperature during operation of the optical detection mechanism to measure the combined signal. This can, for example, involve the use of a temperature-controlled incubator. Alternatively, it is preferred that the optical detection mechanism includes a detector selected from the group consisting of a luminometer and a fluorometer. More preferably, the detector is the luminometer.

In accordance with a second highly preferred embodiment of the generally described apparatus for determining, with process control, the presence or absence of a first analyte in a sample that includes an internal control, the optical detection mechanism is not configured to measure the second analyte signal generated by the second analyte probe. When this is the case, it is preferred that the holder does not substantially change temperature during operation of the optical detection mechanism to measure the combined signal; the first analyte and the internal control each include nucleic acid; and the optical detection mechanism does not measure the first analyte signal without also measuring the internal control signal. Alternatively, the optical detection mechanism does not measure the first analyte signal without also measuring the internal control signal, and the apparatus further includes an output device that produces a tangible record of the determining step performed by the processor. More preferably, the holder does not substantially change temperature during operation of the optical detection mechanism to measure the combined signal; the first analyte and the internal control each include nucleic acid; and the optical detection mechanism does not measure the first analyte signal without also measuring the internal control signal.

When this is the case, it is preferred that the sample maintains substantially constant temperature during operation of the optical detection mechanism to measure the combined signal. Alternatively, it is preferred that the optical detection mechanism includes a detector selected from the group consisting of a luminometer and a fluorometer. More preferably, the detector is the luminometer.

In addition to the foregoing highly preferred embodiments of the generally described apparatus, there also are a number of generally preferred variations that can be used to modify the invented apparatus. In one generally preferred embodiment, the sample is contained in a reaction receptacle, and the holder is configured to contain a plurality of reaction receptacles. More preferably, the reaction receptacle is selected from the group consisting of a tube, and a well of a multiwell plate. In another generally preferred embodiment, the optical detection mechanism includes a detector selected from the group consisting of a luminometer and a fluorometer. More preferably, the detector is the luminometer. In still another generally preferred embodiment, the processor is a computer (e.g., such as a stand-alone computer) that includes a software look-up table. In yet another generally preferred embodiment, the holder does not substantially change temperature during operation of the optical detection mechanism to measure the combined signal; the first analyte, the second analyte, and the internal control each include nucleic acid; and the optical detection mechanism does not measure the first analyte signal without also measuring the internal control signal. In still yet another generally preferred embodiment, the sample maintains substantially constant temperature during operation of the optical detection mechanism to measure the combined signal. More preferably, wherein the holder is contained within a temperature-controlled incubator. In still yet another generally preferred embodiment, the optical detection mechanism does not measure the first analyte signal without also measuring the internal control signal, and the apparatus further includes an output device that produces a tangible record of the determining step performed by the processor.

In another aspect, the invention relates to a method, employing process control, for determining the presence or absence of a first analyte in a sample that includes an internal control. Generally speaking, the method includes a first step (a) for preparing a reaction mixture to be tested for the presence of the first analyte. The reaction mixture includes: the sample; an internal control probe that generates an internal control signal after contacting the internal control; a first analyte probe that generates a first analyte signal after contacting the first analyte, if present in the sample; and optionally a second analyte probe that generates a second analyte signal after contacting a second analyte, if present in the sample. Next, there is a step (b) for measuring: (i) a combined signal generated by the internal control probe and the analyte probe without distinguishing the internal control signal from the analyte signal; and (ii) optionally the second analyte signal generated by the second analyte probe, if included in the reaction mixture. Next, there is a step (c) for determining which of the following situations applies: (i) the sample does not include the first analyte if the magnitude of the combined signal is less than a first analyte cutoff value, and either (1) the magnitude of the combined signal is greater than or equal to a validity cutoff value, or (2) the second analyte probe is included in the reaction mixture, the second analyte signal is measured in step (b), and the magnitude of the second analyte signal measured in step (b) is greater than or equal to a second analyte cutoff value, thereby establishing that the sample includes the second analyte; (ii) the sample includes the first analyte if the magnitude of the combined signal is greater than or equal to the first analyte cutoff value; and (iii) it cannot be determined whether or not the sample includes the first analyte if the magnitude of the combined signal is less than the validity cutoff value, and, if the second analyte probe is included in the reaction mixture, the second analyte signal is measured in step (b), and the magnitude of the second analyte signal measured in step (b) is less than the second analyte cutoff value. Generally, the first analyte cutoff value is a signal amount greater than the validity cutoff value, and the detectable maximum of the internal control signal cannot exceed the first analyte cutoff value.

In accordance with a first highly preferred embodiment of the generally described method, the reaction mixture prepared in step (a) includes the second analyte probe; step (b) includes measuring at a constant temperature; and step (c) is automated by a computer. More preferably, step (b) includes measuring optically. In one instance, step (b) preferably includes measuring optically with a device selected from the group consisting of a luminometer and a fluorometer. More preferably, the device is the luminometer. In another instance, the internal control probe, the first analyte probe, and the second analyte probe are each detectably labeled. More preferably, the internal control probe and the first analyte probe are each detectably labeled with identical detectable labels. For example, the internal control probe and the first analyte probe are each detectably labeled with the same chemiluminescent label. Alternatively, the internal control probe and the first analyte probe are each detectably labeled with the same acridinium ester.

In accordance with a second highly preferred embodiment of the generally described method, the reaction mixture prepared in step (a) does not include the second analyte probe; step (b) includes measuring at a constant temperature; and step (c) is automated by a computer. More preferably, step (b) includes measuring optically. In one instance, step (b) preferably includes measuring optically with a device selected from the group consisting of a luminometer and a fluorometer. More preferably, the device is the luminometer. In another instance, the internal control probe, the first analyte probe, and the second analyte probe are each detectably labeled. More preferably, the internal control probe and the first analyte probe are each detectably labeled with identical detectable labels. For example, the internal control probe and the first analyte probe are each detectably labeled with the same chemiluminescent label. Alternatively, the internal control probe and the first analyte probe are each detectably labeled with the same acridinium ester. In addition to the foregoing highly preferred embodiments of the generally described method, there also are a number of generally preferred variations that can be used to modify the invented method. In one generally preferred embodiment, step (b) includes measuring at a constant temperature, and step (c) is automated by a computer. In another generally preferred embodiment, the reaction mixture prepared in step (a) includes the second analyte probe. More preferably, the second analyte signal is measured in step (b); the magnitude of the second analyte signal measured in step (b) is less than the second analyte cutoff value; and the magnitude of the combined signal measured in step (b) is greater than or equal to the validity cutoff value, thereby determining that the sample does not include the second analyte. In still another generally preferred embodiment, the reaction mixture prepared in step (a) does not include the second analyte probe. More preferably, the magnitude of the combined signal measured in step (b) is less than the first analyte cutoff value but greater than or equal to the validity cutoff value, and it is determined in step (c) that the sample does not include the first analyte. In yet another generally preferred embodiment, each of the first analyte, the internal control, and the second analyte include nucleic acid. In still yet another generally preferred embodiment, the internal control probe, the first analyte probe, and the second analyte probe are each detectably labeled. More preferably, the internal control probe and the first analyte probe are each detectably labeled with identical detectable labels. When this is the case, it is preferred that the internal control probe and the first analyte probe are each detectably labeled with the same chemiluminescent label. Alternatively, it preferred that the internal control probe and the first analyte probe are each detectably labeled with the same acridinium ester. In yet still another generally preferred embodiment, the internal control probe, the first analyte probe, and the second analyte probe each include chemiluminescent labels. In yet still another generally preferred embodiment, step (b) includes measuring optically. More preferably, step (b) includes measuring optically with a device selected from the group consisting of a luminometer and a fluorometer. Still more preferably, the device is the luminometer. In yet still another generally preferred embodiment, step (c) involves determining with a computer that includes a software look-up table. In yet still another generally preferred embodiment, each of the probes includes nucleic acid.

DETAILED DESCRIPTION

Introduction and Overview

The present invention provides tools and methods for identifying analyte-containing samples by detecting an IC signal and an analyte signal in the same reaction mixture using single channel detection, using only a single read, and without needing to distinguish signals contributed by IC and analyte probe binding. In a highly preferred embodiment, a single detectable label species is used to label both the analyte probe, as may be used for detecting analyte amplicons, and the IC probe, as may be used for detecting IC amplicons. In another embodiment, the labels can differ as long as they both can be detected in a single channel of a detection device, and as long as the maximum signal generated by IC detection probe falls below the threshold cutoff for analyte detection. In accordance with the described method, the magnitude of the signal representing detection of analyte and IC is used as a variable, thus requiring a plurality of thresholds for interpreting results. In this way it is possible to eliminate the requirement for either spatial separation or separate labels to detect IC amplicons and analyte amplicons, and to be able to validate a negative result for analyte detection. This is particularly true when probe hybridization is assessed at constant temperature, as illustrated below, thereby distinguishing the disclosed technique from thermal melting analysis. Indeed, the described technique does not require monitoring the extent of probe hybridization under a plurality of temperature conditions.

DEFINITIONS

Figure 1:
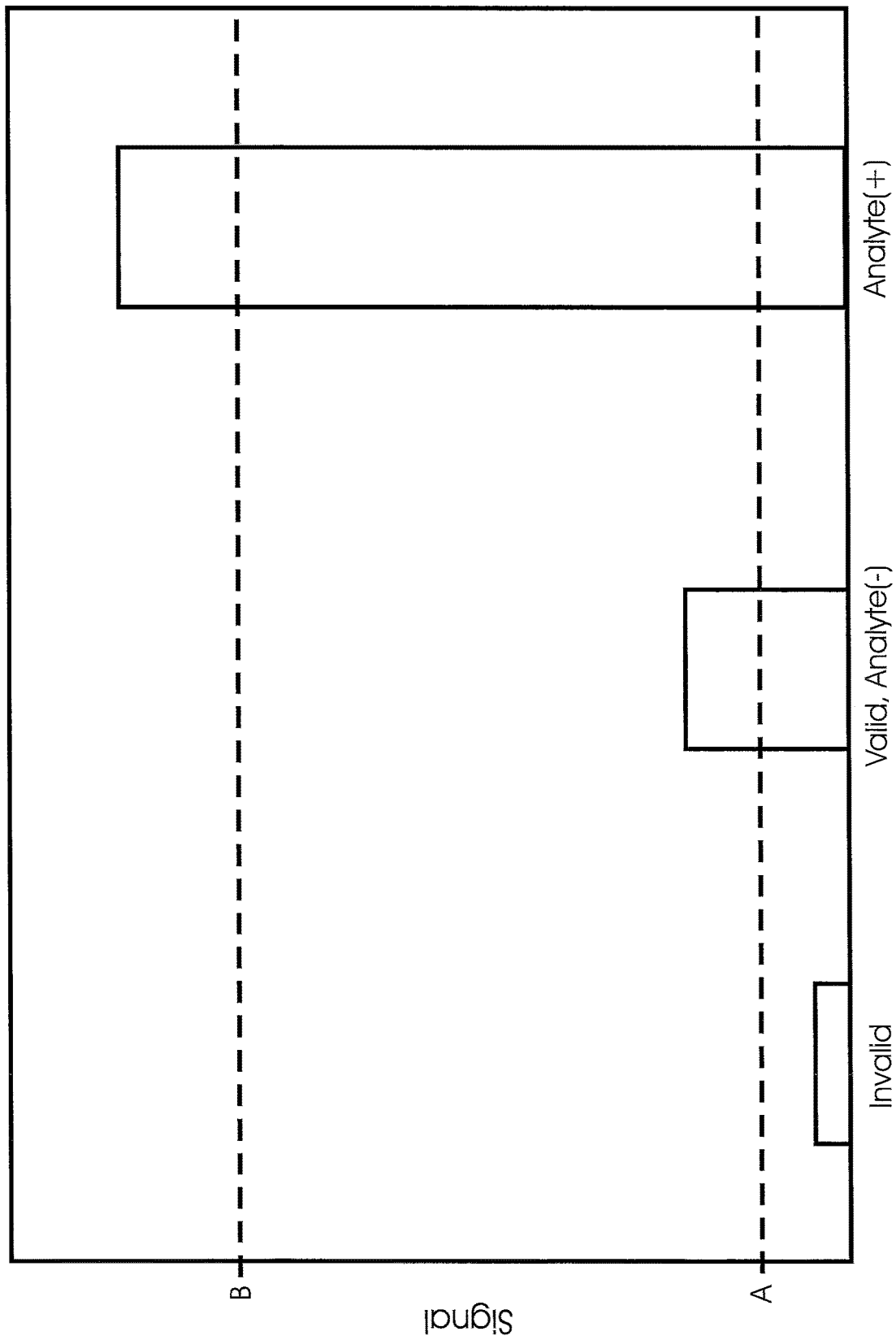
FIG. 1 is a bar graph illustrating how the magnitude of a combined IC signal plus analyte signal is used in accordance with the disclosed technique to determine the presence or absence of analyte in an IC-validated assay. The vertical axis of the graph represents combined signal magnitude. Indicated on the vertical axis are validity ("A") and analyte ("B") cutoffs that are used for interpreting experimental results. A combined signal falling below the validity cutoff cannot indicate valid assay results (i.e., possibly indicating a failed or invalid reaction). A combined signal that meets or exceeds the validity cutoff, but does not meet or exceed the analyte cutoff indicates a valid reaction that did not include analyte. A combined signal that meets or exceeds the analyte cutoff indicates a reaction that included analyte, and is automatically considered valid.

The following terms have the indicated meanings in the specification unless expressly indicated to have a different meaning.

By "sample" or "test sample" is meant any substance suspected of containing a target organism or biological molecule, such as a nucleic acid derived from the target organism. The substance may be, for example, an unprocessed clinical specimen, a buffered medium containing the specimen, a medium containing the specimen and lytic agents for releasing nucleic acid belonging to the target organism, or a medium containing nucleic acid derived from the target organism which has been isolated and/or purified in a reaction receptacle or on a reaction material or device. In some instances, a sample or test sample may comprise a product of a biological specimen, such as an amplified nucleic acid to be detected.

By "analyte" is meant a substance, such as a nucleic acid or protein, that is detected or measured in an analytical procedure. The analyte may be contained in a sample undergoing testing.

As used herein, "standard samples" are samples containing known quantities of an analyte.

As used herein, "polynucleotide" means either RNA, DNA, or a chimeric molecule containing both RNA and DNA.

By "analyte polynucleotide" or "analyte nucleic acid" is meant a polynucleotide of interest that is to be detected or quantified.

By "analyte polynucleotide standard" is meant a known quantity of an analyte polynucleotide, or fragment thereof. For example, a viral analyte polynucleotide standard may contain a known number of copies of a viral genome, viral transcript, or in vitro synthesized transcript representing a portion of the viral genome.

"Nucleic acid" refers to a multimeric compound comprising nucleosides or nucleoside analogs which have nitrogenous heterocyclic bases, or base analogs, which are linked by phosphodiester bonds or other linkages to form a polynucleotide. Nucleic acids include RNA, DNA, or chimeric DNA-RNA polymers, and analogs thereof. A nucleic acid "backbone" may be made up of a variety of linkages, including one or more of sugar-phosphodiester linkages, peptide-nucleic acid (PNA) bonds (PCT No. WO 95/32305), phosphorothioate linkages, methylphosphonate linkages, or combinations thereof. Sugar moieties of the nucleic acid may be either ribose or deoxyribose, or similar compounds having known substitutions, such as 2' methoxy substitutions and 2' halide substitutions (e.g., 2'-F). Nitrogenous bases may be conventional bases (A, G, C, T, U), analogs thereof (e.g., inosine), derivatives of purine or pyrimidine bases, such as $N^4$-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo[3,4-d]pyrimidine (U.S. Pat. Nos. 5,378,825, 6,949,367 and PCT No. WO 93/13121). Nucleic acids may include "abasic" positions in which the backbone does not include a nitrogenous base for one or more residues (see U.S. Pat. No. 5,585,481). Nucleic acids also include "locked nucleic acids" (LNA), an analog containing one or more LNA nucleotide monomers with a bicyclic furanose unit locked in an RNA mimicking sugar conformation (Vester et al., 2004, *Biochemistry* 43(42):13233-41). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Methods for synthesizing nucleic acids in vitro are well known in the art.

By "oligonucleotide" or "oligomer" is meant a polymer made up of two or more nucleoside subunits or nucleobase subunits coupled together. Oligonucleotides preferably have a length in the range of from 10-100 nucleotides, more preferably 10-80 nucleotides, and still more preferably from 15-60 nucleotides. The oligonucleotide may be DNA and/or RNA and analogs thereof. The sugar groups of the nucleoside subunits may be ribose, deoxyribose and analogs thereof, including, for example, ribonucleosides having a 2'-O-methylsubstitution to the ribofuranosyl moiety. Oligonucleotides including nucleoside subunits having 2' substitutions and which are useful as detection probes, capture oligos and/or amplification oligonucleotides are disclosed by Becker et al., in U.S. Pat. No. 6,130,038. The nucleoside subunits may be joined by linkages such as phosphodiester linkages, modified linkages, or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo-peptide backbone, such as a 2-aminoethylglycine backbone which couples the nucleobase subunits by means of a carboxymethyl linker to the central secondary amine (DNA analogs having a pseudo-peptide backbone are commonly referred to as "peptide nucleic acids" or "PNA", and are disclosed by Nielsen et al., "Peptide Nucleic Acids," U.S. Pat. No. 5,539,082.) Other non-limiting examples of oligonucleotides or oligomers contemplated by the present invention include nucleic acid analogs containing bicyclic and tricyclic nucleoside and nucleotide analogs referred to as "Locked Nucleic Acids,"

"Locked Nucleoside Analogues" or "LNA." (Locked Nucleic Acids are disclosed by Wang, "Conformationally Locked Nucleosides and Oligonucleotides," U.S. Pat. No. 6,083,482; Imanishi et al., "Bicyclonucleoside and Oligonucleotide Analogues," U.S. Pat. No. 6,268,490; and Wengel et al., "Oligonucleotide Analogues," U.S. Pat. No. 6,670,461.) Any nucleic acid analog is contemplated by the present invention, provided that the modified oligonucleotide can hybridize to a target nucleic acid under either stringent hybridization conditions or amplification reaction conditions.

As used herein, "amplification" or "amplifying" refers to an in vitro procedure for obtaining multiple copies of a target nucleic acid sequence, its complement or fragments thereof. For example, an in vitro amplification reaction is an enzyme-catalyzed reaction that results in the synthesis of multiple copies of a target nucleic acid sequence, its complement or fragments thereof. Examples of amplification methods that can be used for preparing in vitro amplification reactions are given below. Preferred in vitro amplification reactions synthesize amplicons in an exponential fashion, meaning that one amplicon serves as the template for production of new amplicons.

By "amplicon" or "amplification product" is meant a nucleic acid molecule generated in a nucleic acid amplification reaction. An amplicon or amplification product contains a target nucleic acid sequence that may be of the same or opposite sense as the target nucleic acid.

By "analyte amplicon" or "analyte amplification product" is meant an amplicon synthesized using an analyte nucleic acid as the template in a nucleic acid amplification reaction.

As used herein, "probe" refers to an analyte-specific reagent useful for detection of a target, such as a target biological molecule. Examples of probes include nucleic acid hybridization probes, antibody probes, cell surface receptors, and receptor-specific ligands.

By "hybridization" or "hybridize" is meant the ability of two completely or partially complementary nucleic acid strands to come together under specified hybridization assay conditions to form a stable structure having a double-stranded region. The two constituent strands of this double-stranded structure, sometimes called a "hybrid," are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art.

As used herein, a "hybridization probe" is an oligonucleotide that hybridizes specifically to a target sequence in a nucleic acid, preferably in an amplified nucleic acid, under conditions that promote hybridization, to form a detectable hybrid. A probe optionally may contain a detectable moiety which either may be attached to the end(s) of the probe or may be internal. The nucleotides of the probe which combine with the target polynucleotide need not be strictly contiguous, as may be the case with a detectable moiety internal to the sequence of the probe. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). The "target" of a probe generally refers to a sequence contained within an amplified nucleic acid sequence which hybridizes specifically to at least a portion of a probe oligonucleotide using standard hydrogen bonding (i.e., base pairing). A probe may comprise target-specific sequences and optionally other sequences that are non-complementary to the target sequence that is to be detected.

As used herein, a "detectable label," or simply "label," is a chemical moiety that can be detected, or can lead to a detectable response. Detectable labels in accordance with the invention can be linked to probes, such as hybridization probes, either directly or indirectly. Examples of preferred detectable labels include radioisotopes, enzymes, haptens, chromophores such as dyes or particles that impart a detectable color (e.g., latex beads or metal particles), luminescent compounds (e.g., bioluminescent, phosphorescent or chemiluminescent moieties) and fluorescent compounds.

As used herein, "homogeneous detectable label" refers to a label that can be detected in a homogeneous fashion by determining whether the label is on a probe bound to a target sequence. That is, homogeneous detectable labels can be detected without physically removing bound (e.g., hybridized) from non-bound (e.g. unhybridized) forms of the label or labeled probe. Homogeneous detectable labels are preferred when using labeled probes for detecting nucleic acids. Examples of homogeneous labels have been described in detail by Arnold et al., U.S. Pat. No. 5,283,174; Woodhead et al., U.S. Pat. No. 5,656,207; and Nelson et al., U.S. Pat. No. 5,658,737. Preferred labels for use in homogenous assays include chemiluminescent compounds (e.g., see Woodhead et al., U.S. Pat. No. 5,656,207; Nelson et al., U.S. Pat. No. 5,658,737; and Arnold, Jr., et al., U.S. Pat. No. 5,639,604). Preferred chemiluminescent labels are acridinium ester ("AE") compounds, such as standard AE or derivatives thereof (e.g., naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE).

A "homogeneous assay" refers to a detection procedure that does not require physical separation of bound probe from non-bound probe prior to determining the extent of specific probe binding. Exemplary homogeneous assays, such as those described herein, can employ molecular torches, molecular beacons or other self-reporting probes which have a stem-and-loop structure and emit fluorescent signals when hybridized to an appropriate target, chemiluminescent acridinium ester labels which can be selectively destroyed by chemical means unless present in a hybrid duplex, and other homogeneously detectable labels that will be familiar to those having an ordinary level of skill in the art.

In the context of the invention, certain methods are used for making or outputting a diagnostic determination. For example, based on a set of data there will be a conclusion that the likelihood of a particular analyte being present in a test sample is very high. An output result of the method can be indicated as a step for "determining" or "assigning" or "establishing" or "calling" that a particular analyte is present, or perhaps absent.

As used herein, an "internal control" is an agent included in a reaction mixture that is used for detecting the presence or absence of an analyte, where detection of the internal control, directly or indirectly, serves to validate assay process steps. In the context of an assay that detects a nucleic acid analyte using an amplification reaction, an internal control can be a nucleic acid template that can be co-amplified and detected in a hybridization reaction along with the nucleic acid analyte. Detection of internal control amplification products at an appropriate level confirms success of the amplification and hybridization process steps. In one embodiment, an internal control nucleic acid amplifies using the same primers that amplify analyte nucleic acid, but internal control amplicons and analyte amplicons are detected using different hybridization probes. Preferred internal controls include exogenous agents that are added to reaction mixtures used for detecting the presence or absence of analytes.

By "internal control amplicon" or "IC amplicon" or "IC amplification product" or variants thereof is meant an amplicon synthesized using an internal control nucleic acid as the template in a nucleic acid amplification reaction.

As used herein, "apparatus" refers to the things necessary to carry out a purpose or for a particular use.

As used herein, a "holder" is a structural element for keeping something in place. For example, a holder may contain a tube, a multiwell plate, a capillary, or other reaction vessel. The holder may include mechanical clips to retain the thing being held. Preferably, the holder of an apparatus useful for performing the invented assays will permit optical access between a sample being held, such as a liquid-phase reaction mixture, and an optical detection mechanism.

As used herein, an "optical detection mechanism" refers to the collection of components necessary for collecting optical signals from a sample undergoing testing. Preferred examples of useful optical detection mechanisms include fluorometers and luminometers.

As used herein a "channel" of an energy sensor device, such as a device equipped with an optical energy sensor, refers to a defined band of wavelengths that can be detected or quantified to the exclusion of other bands of wavelengths. For example, one detection channel of a luminometer might be capable of detecting light energy emitted by one or more chemiluminescent labels over a range of wavelengths as a single event. Light emitted during a chemiluminescent reaction can be quantified by a luminometer using relative light units (RLU), a unit of measurement indicating the relative number of photons emitted by the sample at a given wavelength or band of wavelengths. Light emitted as the result of fluorescence can be quantified as relative fluorescence units (RFU) at a given wavelength, or over a band of wavelengths.

As used herein, "single-channel detection" refers to a process whereby one or more signals can be detected within a defined band of wavelengths represented by one channel of an energy sensor device. If, for example, two detectable labels, each disposed on a different probe, both emit light of characteristic wavelengths different from each other, and if those wavelengths are detected within a defined band of wavelengths corresponding to one detection channel of an energy sensor device, then the detection would be described as "single channel detection." By single channel detection there is no distinction between which label produced the photon being detected when the photons arise from different labels, and have wavelengths falling within the detection range of the single detection channel.

As used herein, "single-read determination" refers to the process of obtaining results from a detection step following a binding reaction between a probe and an analyte. By single-read determination it is unnecessary to change reaction conditions, such as probe hybridization conditions, or to perform a secondary hybridization reaction.

As used herein, an "internal control signal" (sometimes referred to as an "IC signal") is a measurable signal indicating the presence of an internal control, or product thereof (e.g., such as an amplification product) in a reaction mixture. The IC signal may be produced directly by the internal control, for example if the internal control is labeled. Alternatively, the internal control signal may be produced by a probe (e.g., an internal control probe) that specifically interacts with the internal control or product thereof. Preferred internal controls include proteins and nucleic acids.

As used herein, an "analyte signal" is a measurable signal indicating the presence of an analyte, or product thereof (e.g., such as an amplification product) in a reaction mixture. The analyte signal may be produced directly by the analyte, for example if the analyte is labeled. Alternatively, the analyte signal may be produced by a probe (e.g., an analyte probe) that specifically interacts with the analyte. Preferred analytes include proteins and nucleic acids.

As used herein, a "combined signal value" is a single value indicating the combination of detectable signals measured for an analyte and an IC in a single reaction mixture. A combined signal does not distinguish the internal control signal from the analyte signal. For example, a combined signal value may be reported in RLU (relative light units) for chemiluminescent label(s), or in RFU (relative fluorescence units) for fluorescent label(s).

In certain multiplex assays that detect more than one analyte, the different analytes may be detected by detecting or measuring, respectively, a "first analyte signal" and a "second analyte signal." The presence or absence of the different analytes may be judged by comparing the magnitudes of the respective signals with respective cutoff values (e.g., "first" and "second" analyte cutoff values).

As used herein, a "threshold" or "threshold cutoff" or simply "cutoff" refers to a quantitative limit used for interpreting experimental results, where results above and below the cutoff lead to opposite conclusions. For example, a measured signal falling below a cutoff may indicate the absence of a particular target, but a measured signal that exceeds the same cutoff may indicate the presence of that target. By convention, a result that meets a cutoff (i.e., has exactly the cutoff value) is given the same interpretation as a result that exceeds the cutoff.

As used herein, a "validity cutoff value" is a cutoff value used for determining whether or not a process step is valid (e.g., valid or invalid). For example, an internal control signal that meets or exceeds a validity cutoff may indicate the process functioned as expected, and that results of an assay incorporating that process are valid. Conversely, an internal control signal falling below the validity cutoff may indicate the process did not function as expected, and that results of the assay are invalid.

As used herein, an "analyte cutoff value" is a cutoff value used for indicating the presence or absence of an analyte in a reaction mixture or test sample. For example, an analyte signal that meets or exceeds an analyte cutoff may indicate the presence of the analyte in a reaction mixture or test sample. Conversely, an analyte signal falling below the analyte cutoff, if validated by process control, would indicate the absence of the analyte.

As used herein, a "look-up table" refers to a collection of possible combinations of positive and negative results expressed relative to (e.g., < or ≥) a threshold cutoff value. Combinations in the collection may be associated with an interpretation that assigns positive or negative status to the presence of an analyte in a sample undergoing testing. Assay validity status also can be assigned. A look-up table can be stored on computer-readable media, and conventionally is used for decoding experimental results.

By "kit" is meant a packaged combination of materials, typically intended for use in conjunction with each other.

Kits in accordance with the invention may include instructions or other information in a "tangible" form (e.g., printed information, electronically recorded on a computer-readable medium, or otherwise recorded on a machine-readable medium such as a barcode for storing numerical values).

PREFERRED EMBODIMENTS

The analytical technique described herein, in certain respects, goes opposite earlier approaches used by many others. For example, unlike the above-referenced U.S. Pat. No. 6,586,234, which describes IC validation using a two-read approach that differentiates (a) analyte signal from (b) the combination of analyte signal and IC signal, the present approach never isolates these signals. More specifically, the present approach employs a single read method that does not require attributing the origin or magnitude of signal arising from IC and analyte probes, even when the signals are detected using a single detection channel of a detection device, as may result from the use of identical labels on the two probes. Indeed, the present technique uses single-channel detection for simultaneously detecting, in a single reaction mixture, signals produced by both the IC probe and the analyte probe. The present technique does not separate IC and analyte probes in separate detection reactions, but instead combines the probes, and detects signals arising therefrom simultaneously. Again, the IC and analyte probes advantageously can harbor either the same detectable label, or different labels that are detected using a single channel of a detection device. Where others may use a single cutoff for detecting signals from multiple targets detected using the same label, the present technique requires the use of separate cutoffs (e.g., so-called validity cutoff, and analyte cutoff). Use of the plurality of separate cutoffs permits avoidance of separate reads to distinguish signals arising from the different probes. In accordance with the present technique, there are a plurality of threshold cutoffs, and there is a requirement that the magnitude of signal arising from detection of IC probe cannot exceed the cutoff used for indicating the presence of analyte. Stated differently, the maximum detectable IC signal cannot exceed the cutoff used for indicating the presence of analyte. In aggregate, these differences distinguish the present technique from earlier approaches.

Generally speaking, the techniques disclosed herein can be applied to detection of a variety of analytes, including: nucleic acids (e.g., DNA and RNA), proteins (e.g., antibodies, receptors for hormones or other ligands, etc.), as well as other molecules of biological interest. Particularly preferred analytes for identification by the disclosed methods are nucleic acids that are detected using complementary hybridization probes. The IC preferably is an exogenous, synthetic nucleic acid that is included in a reaction mixture being tested for the presence of analyte nucleic acid prior to co-amplification with analyte nucleic acid. Separate hybridization probes having different base sequences are used for detecting analyte and IC amplicons. The detection step is carried out at constant temperature. In a highly preferred embodiment, the different probes having specificity for the different target nucleic acids (i.e., IC and analyte) are labeled with the same chemical species of detectable label. However, if different detectable labels are used for labeling the different probes, signals produced by the different labels must be detectable using a single channel of a detection device. Preferably, both detectable labels produce optical signals that are detected using a single channel of a detection device, where the channel is defined by a predetermined wavelength range.

Thresholds

One aspect of the present invention relates to the definition and use of a plurality of threshold cutoffs for detectable signals that are used for identifying the presence or absence of an analyte in an assay validated by an IC. Preferably, when IC and analyte are detected using different probes that harbor the same chemical species of detectable label, there are two threshold cutoffs for a signal detected in a single channel of a detection instrument that detects analyte signal and IC signal. The lower of the two threshold cutoffs (i.e., the "validity cutoff") is used for validating the IC process control. The upper of the two threshold cutoffs is used for indicating the presence or absence of analyte in the sample undergoing testing. A signal that fails to meet or exceed the value of the validity cutoff indicates an invalid reaction due to failure of the assay process. Such a situation may result from inhibition of an amplification step and/or detection step of the assay. A signal that exceeds the validity cutoff, but does not meet or exceed the threshold cutoff for analyte detection indicates success of the amplification and detection steps of the assay, and further indicates the absence of analyte from the sample. This latter result can be scored as "valid, analyte-negative" by the method disclosed herein. Finally, detection of a signal that exceeds both the validity cutoff and the analyte threshold cutoff indicates the presence of analyte in the sample (i.e., an "analyte-positive" sample). When this is the case, there is no need to report or question validity of the assay result. These features of the invention are illustrated in FIG. 1.

Success of the technique disclosed herein depends on certain general relationships between the allowable magnitudes of the signals representing detection of IC and analyte, and the plurality of threshold cutoffs. Importantly, the validity cutoff must be distinct from, and lower than the threshold cutoff for analyte detection when the analyte and IC are detected using different probes harboring detectable labels that produce signals detectable in a single channel of a detection device. In a highly preferred embodiment, the detectable labels are the same detectable label (e.g., the same chemical species of fluorescent label, or chemiluminescent label, such as an AE label). Indeed, signal resulting from amplification and detection of IC that exceeds the validity cutoff should not ambiguously indicate the presence of analyte detected using probes harboring the same chemical species of detectable label. This may be ensured, for example, by requiring that the magnitude of the signal resulting from detection of IC amplicons only (i.e., no analyte being present in the reaction) has an upper limit threshold that cannot be exceeded. In a particularly preferred approach, this is accomplished by ensuring that the IC amplification and detection component of the disclosed assays are calibrated so that the IC signal cannot exceed the upper limit threshold cutoff in amplification reaction that contains no analyte. This prevents false-positive results indicating the presence of analyte due to amplification and detection of the IC only. The threshold cutoff for detection of analyte is always greater than the validity cutoff. Detection of a signal that meets or exceeds the threshold cutoff for analyte detection automatically validates the analyte-positive assay result.

Many different approaches can be used to ensure that the maximum signal arising from IC detection (e.g., detection of IC amplicons) is below the threshold cutoff for detection of analyte, when IC and analyte are detected using a single chemical species of detectable label, or different detectable labels that can be detected using a single channel of a detection device. For example, the specific activity (e.g., measurable as units of detectable label per unit mass of probe) for IC amplicons can be reduced relative to the specific activity of probe used for detecting analyte amplicons. The amount or concentration of IC-specific probe used in the hybridization reaction can be reduced relative to the amount or concentration of analyte-specific probe. The label disposed on the IC-specific probe can be selected to be less efficiently detected relative to the label disposed on the analyte-specific probe. In a highly preferred embodiment, the different probes used for detecting IC amplicons and analyte amplicons are labeled with the same chemical species of detectable label (e.g., a chemiluminescent label such as an acridinium ester label of a particular structure, or alternatively a fluorescent label of a particular structure), and the amount of IC-specific probe used for detecting IC amplicons is less than the amount of analyte-specific probe used for detecting analyte amplicons. Of course, input amounts of IC template nucleic acid used in co-amplification reactions also can be adjusted so that the magnitude of the hybridization signal arising from detection of IC amplicons is below the value of the analyte cutoff. For example, the input amount of IC nucleic acid may be chosen to be no greater than ten times the lower limit of detection for analyte, more preferably no greater that three times the lower limit of detection for analyte, more preferably no greater than two times the lower limit of detection for analyte, and still more preferably no greater than the lower limit of detection for analyte. For example, the amount of IC template nucleic acid used in an amplification reaction preferably falls in the range of from one-half to ten times the lower limit of detection for analyte in the assay, still more preferably in the range of from one-tenth to one times the lower limit of detection for analyte in the assay. Combinations of any of these low input levels of IC template, together with any of the above-described controlled amounts of probe also have been used successfully, and are within the scope of the present disclosure.

The foregoing discussion of threshold cutoffs is relevant to analysis of IC and analyte when those targets are detected using a single chemical species as the detectable label (e.g., same chemiluminescent label, same fluorescent label, etc.), or different chemical species of detectable labels that can be detected using a single channel of a detection device. Analysis of results obtained by this approach is illustrated in Table 1. Detection of a second analyte using a detectable label different from the one(s) used for detecting IC and the first analyte can be accomplished, and may involve the use of a different threshold cutoff. Indeed, the threshold cutoff used for assessing the presence or absence of the second analyte can be independent of the threshold cutoffs used for assessing results for the first analyte and IC. Analysis of results obtained by this latter approach is illustrated in Table 2.

Certain Relationships Among Signal Magnitudes and Threshold Cutoffs

As stated elsewhere herein, there are a number of meaningful relationships among the magnitudes of signals representing detection of internal control and one or more analytes, and various respective threshold cutoffs. For example, in the context of an assay, and apparatus for performing the assay, that includes an internal control and first analyte, optionally including a second analyte, the magnitude of a measured combined signal (e.g., produced by an internal control probe and first analyte probe) can be compared with a validity cutoff value and with a first analyte cutoff value. If the assay includes measurement of a second analyte signal (e.g., being produced by a second analyte probe, and being distinguishable from the combined signal), then that second analyte signal can be compared with a second analyte cutoff value. If the magnitude of the combined signal is greater than or equal to the validity cutoff value it is established by process control that assay results are valid. If the magnitude of the combined signal is greater than or equal to the first analyte cutoff value it is established that the first analyte is detected. If the magnitude of the combined signal is less than the validity cutoff value it is not established by process control that assay results are valid. If the reaction mixture includes the second analyte probe, and if the magnitude of the second analyte signal is greater than or equal to the second analyte cutoff value it is established by process control that assay results are valid, and established that the second analyte is detected. If the reaction mixture includes the second analyte probe, and if the magnitude of the second analyte signal is less than the second analyte cutoff value it is not established that the second analyte is detected, and it is not established by process control that assay results are valid. Thus, when the second analyte signal is detected, that signal also can serve to validate assay results, including negative results for detection of the first analyte. Each of these determinations may be established by a processor or computer component of an apparatus according to the invention.

Examples of Threshold Establishment

Comparisons between threshold cutoffs (i.e., validity cutoff, and analyte cutoff) and measured test signals representing combined signals for detection of IC plus analyte can be implemented by alternative approaches. In one preferred embodiment, predetermined threshold cutoffs are used for assessing test results and determining whether analyte is present or absent. In a different preferred embodiment, threshold cutoffs are established using calibrators run on each different machine that is to be used for testing.

Establishing threshold cutoffs specific for a particular machine and/or set of reagents may be carried out in different ways, but generally will employ one or more calibrator standards (i.e., one or more standards containing known amounts of relevant nucleic acid to be amplified and detected). Each calibration reaction includes the internal control. A "negative" calibrator can be used for establishing a validity cutoff that must be exceeded by a signal representing detection of IC and analyte for an assay to be regarded as valid. The negative calibrator reaction preferably includes IC template nucleic acid that can be amplified and detected, but does not include any analyte nucleic acid. One approach for establishing the value of the validity cutoff is to calculate one-half (i.e., 50%) of the value of a signal measured in a negative calibrator run (i.e., amplification and detection procedure), or more preferably one-half of the value of an average of signals measured in a plurality of negative calibrator amplification and detection reactions. Any test reaction yielding a combined signal value below this validity cutoff would be regarded as invalid (i.e., indicating process failure) in the absence of validating results measured for a second analyte. Fractions of the negative calibrator results other than one-half (e.g., 60%, 70%, etc.) may be alternatively be chosen as the validity cutoff with good results. Any test reaction yielding a signal value above the validity cutoff would be regarded as valid.

The upper threshold (i.e., the "analyte cutoff") that must be exceeded for a result to be regarded as positive for analyte (i.e., "analyte-positive") in its simplest form also can be determined from the result obtained using the negative calibrator reaction. The analyte cutoff preferably will be at least one and one-half times the value of the signal measured for the negative calibrator trial (or the average of negative calibrator runs). More preferably, the analyte cutoff will be at least two times the value of the signal measured for the negative calibrator trial. Still more preferably, the analyte cutoff is determined using results from negative calibrator trials, as well as from positive calibrator trials. For example, an analyte cutoff can be determined by increasing the value of a multiple of the negative calibrator by a fractional amount (e.g., 10%, 20%, 30%, or in the range of from 10%-30%) of the value measured for a positive calibrator that yields a signal representing detection of IC and analyte, where both targets are detected using single channel detection. This is illustrated in the Example, below.

Detection of Nucleic Acids

In a preferred embodiment, nucleic acid amplicons are detected in solution using solution-phase hybridization probes that are not immobilized to a solid support when the hybridization signal is detected. This is clearly different from arrayed detection formats, such as nucleic acid microarrays, where interpretation of probe hybridization results depends on spatial separation of one probe from another. As well, the invented method can be practiced using an IC probe and an analyte probe (e.g., each of these being a nucleic acid hybridization probe) that harbor identical chemical species of detectable label, or labels that are similar enough to permit detection using a single detection channel in a detection device. Notably, preferred procedures do not involve detection of a signal representing the presence of analyte only, without also detecting a signal representing the presence of IC. Likewise, preferred procedures do not involve detection of a signal representing the presence of IC only, to the exclusion of analyte, when analyte also is available for detection. For example, in certain embodiments there is detected a cumulative signal indicating the presence of both IC and analyte, meaning that IC signal and analyte signal are not detected separately. In this way, the present method differs from certain other assay formats wherein analyte signal and IC signal are detected separately.

Look-Up Tables

The method described herein conveniently can employ a look-up table for interpreting results and determining the presence or absence of analyte in a sample, as well as for validating assay integrity. Table 1 represents a basic look-up table useful for interpreting results in accordance with the disclosed method of detecting analyte and IC using single channel detection of analyte and IC signals, as may be provided by different probes (i.e., separate probes for IC and analyte) labeled with a single type of detectable label (i.e., identical labels on each probe). With reference to the arrangement of threshold cutoffs, detection of a signal that is below the threshold cutoff for analyte and also below the validity cutoff indicates that the test is invalid. Conversely, detection of a signal that is below analyte cutoff, but above the validity cutoff indicates that the test is valid, and analyte-negative. Finally, a signal that is above the analyte cutoff indicates the test is analyte-positive. Thus, using as few as two probes harboring the same chemical species of detectable label can provide insight into validity of an analytical process, as well as insight into the presence or absence of an analyte.

TABLE 1

Analysis of Results Obtained Using a Single Label Species for Detecting IC and Analyte Signal Evaluation

| Magnitude of Signal Compared to Cutoff for Detection of Analyte | Magnitude of Signal Compared to Validity Cutoff | Result for Analyte |
| --- | --- | --- |
| ≥Analyte cutoff | >Validity cutoff, since analyte cutoff is higher than validity cutoff | Positive |
| <Analyte cutoff | ≥Validity cutoff | Negative |
|  | <Validity cutoff | Invalid Assay |

Multiplexing Advantages and Look-Up Tables

Another advantage of using signal magnitude (e.g., hybridization signal magnitude) as a variable for distinguishing invalid reactions, valid reactions indicating analyte-negative samples, and reactions indicating analyte-positive samples relates to the ability to detect multiple analytes using only a small number of detectable labels. For example, when first analyte (Analyte-1) and IC nucleic acid templates are co-amplified and detected using different probes, each probe harboring a label that can be detected using a first detection channel of a detection device (e.g., the first detectable labels being identical to each other), an unrelated target (Analyte-2) can be detected using a probe harboring a different detectable label, where that different label can be distinguished from the labels used on the Analyte-1 and IC probes (e.g., by kinetic resolution, or by detection using a second detection channel of the detection device, etc). When this is the case, a positive result for detection of Analyte-2 may also serve to validate assay results. As well, Analyte-2 may be positively detected when the detected signal meets or exceeds a second analyte threshold, which may be the same or different from the threshold cutoff that must be met or exceeded to establish the presence of Analyte-1 in the sample. Thus, detection of a signal that exceeds the threshold cutoff for detection of Analyte-2 can validate the assay result (i.e., indicate that the assay components functioned as intended). In accordance with the method, even in the absence of a detectable signal indicating hybridization of the Analyte-1 and IC probes, an Analyte-2 signal that meets or exceeds the threshold cutoff for detection of Analyte-2 can indicate the sample undergoing testing included Analyte-2, but not Analyte-1, and that the assay results are valid (i.e., valid, Analyte-1 negative; Analyte-2 positive). The logical analysis of results from a simple multiplex assay that includes Analyte-1 and IC probes labeled with a commonly detectable label(s) (i.e., the labels on the two probes being detectable using the same detection channel in a detection device), together with an Analyte-2 probe labeled with a second detectable label that is distinguishable from the first label, is presented below in the form of a look-up table (see Table 2).

TABLE 2

Analysis of Results Obtained Using Two Label Species for Detecting IC and Two Analytes

| Magnitude of Signal 2 Compared to Cutoff for Detection of Analyte-2 | Signal 1 Evaluation | | Result for Analyte-1 | Result for Analyte-2 |
|---|---|---|---|---|
| | Magnitude of Signal1 Compared to Cutoff for Detection of Analyte-1 | Magnitude of Signal 1 Compared to Validity Cutoff | | |
| ≥Analyte-2 cutoff | <Analyte-1 cutoff | Valid whether signal 1 is ≥ or < since high signal 2 validates process control | Negative | Positive |
| | ≥Analyte-1 cutoff | Valid since Analyte-1 cutoff is higher than validity cutoff | Positive | Positive |
| <Analyte-2 cutoff | ≥Analyte-1 cutoff | | Positive | Negative |
| | <Analyte-1 cutoff | ≥Validity cutoff <Validity cutoff | Negative Invalid | Negative |

Useful Probe Labeling Systems and Detectable Moieties

Essentially any labeling and detection system that can be used for monitoring specific binding between a probe and an analyte can be used in conjunction with the present invention. Included among the collection of useful labels are radiolabels, enzymes, haptens, linked oligonucleotides, chemiluminescent molecules, fluorescent moieties (either alone or in combination with "quencher" moieties), and redox-active moieties that are amenable to electronic detection methods. Preferred chemiluminescent molecules include acridinium esters of the type disclosed by Arnold et al., in U.S. Pat. No. 5,283,174 for use in connection with homogenous protection assays, and of the type disclosed by Woodhead et al., in U.S. Pat. No. 5,656,207 for use in connection with assays that quantify multiple targets in a single reaction. The disclosures contained in these patent documents are hereby incorporated by reference. Preferred electronic labeling and detection approaches are disclosed in U.S. Pat. Nos. 5,591,578 and 5,770,369, and the published international patent application WO 98/57158, the disclosures of which are hereby incorporated by reference. Redox active moieties useful as labels in the present invention include transition metals such as Cd, Mg, Cu, Co, Pd, Zn, Fe and Ru.

Particularly preferred detectable labels for probes in accordance with the present invention are detectable in homogeneous assay systems (i.e., where, in a mixture, bound labeled probe exhibits a detectable change, such as stability or differential degradation, compared to unbound labeled probe). While other homogeneously detectable labels, such as fluorescent labels and electronically detectable labels, are intended for use in the practice of the present invention, a preferred label for use in homogenous assays is a chemiluminescent compound (e.g., as described by Woodhead et al., in U.S. Pat. No. 5,656,207; by Nelson et al., in U.S. Pat. No. 5,658,737; or by Arnold et al., in U.S. Pat. No. 5,639,604). Particularly preferred chemiluminescent labels include acridinium ester ("AE") compounds, such as standard AE or derivatives thereof, such as naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE.

In some applications, probes exhibiting at least some degree of self-complementarity are desirable to facilitate detection of probe:target duplexes in a test sample without first requiring the removal of unhybridized probe prior to detection. By way of example, structures referred to as "Molecular Torches" are designed to include distinct regions of self-complementarity (coined "the target binding domain" and "the target closing domain") which are connected by a joining region and which hybridize to one another under predetermined hybridization assay conditions. When exposed to denaturing conditions, the two complementary regions (which may be fully or partially complementary) of the Molecular Torch melt, leaving the target binding domain available for hybridization to a target sequence when the predetermined hybridization assay conditions are restored. Molecular Torches are designed so that the target binding domain favors hybridization to the target sequence over the target closing domain. The target binding domain and the target closing domain of a Molecular Torch include interacting labels (e.g., fluorescent/quencher) positioned so that a different signal is produced when the Molecular Torch is self-hybridized as opposed to when the Molecular Torch is hybridized to a target nucleic acid, thereby permitting detection of probe:target duplexes in a test sample in the presence of unhybridized probe having a viable label associated therewith. Molecular Torches are fully described in U.S. Pat. No. 6,361,945, the disclosure of which is hereby incorporated by reference.

Another example of a self-complementary hybridization assay probe that may be used in conjunction with the invention is a structure commonly referred to as a "Molecular Beacon." Molecular Beacons comprise nucleic acid molecules having a target complementary sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular Beacons are fully described in U.S. Pat. No. 5,925,517, the disclosure of which is hereby incorporated by reference.

Molecular beacons preferably are labeled with an interactive pair of detectable labels. Examples of detectable labels that are preferred as members of an interactive pair of labels interact with each other by FRET or non-FRET energy transfer mechanisms. Fluorescence resonance energy transfer (FRET) involves the radiationless transmission of energy quanta from the site of absorption to the site of its utilization in the molecule, or system of molecules, by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred. In addition to FRET, there are at least three other "non-FRET" energy transfer processes by which excitation energy can be transferred from a donor to an acceptor molecule.

When two labels are held sufficiently close that energy emitted by one label can be received or absorbed by the second label, whether by a FRET or non-FRET mechanism, the two labels are said to be in "energy transfer relationship" with each other. This is the case, for example, when a molecular beacon is maintained in the closed state by formation of a stem duplex, and fluorescent emission from a fluorophore attached to one arm of the probe is quenched by a quencher moiety on the opposite arm.

Highly preferred label moieties for the invented molecular beacons include a fluorophore and a second moiety having fluorescence quenching properties (i.e., a "quencher"). In this embodiment, the characteristic signal is likely fluorescence of a particular wavelength, but alternatively could be a visible light signal. When fluorescence is involved, changes in emission are preferably due to FRET, or to radiative energy transfer or non-FRET modes. When a molecular beacon having a pair of interactive labels in the closed state is stimulated by an appropriate frequency of light, a fluorescent signal is generated at a first level, which may be very low. When this same probe is in the open state and is stimulated by an appropriate frequency of light, the fluorophore and the quencher moieties are sufficiently separated from each other that energy transfer between them is substantially precluded. Under that condition, the quencher moiety is unable to quench the fluorescence from the fluorophore moiety. If the fluorophore is stimulated by light energy of an appropriate wavelength, a fluorescent signal of a second level, higher than the first level, will be generated. The difference between the two levels of fluorescence is detectable and measurable. Using fluorophore and quencher moieties in this manner, the molecular beacon is only "on" in the "open" conformation and indicates that the probe is bound to the target by emanating an easily detectable signal. The conformational state of the probe alters the signal generated from the probe by regulating the interaction between the label moieties. Examples of donor/acceptor label pairs that may be used in connection with the invention, making no attempt to distinguish FRET from non-FRET pairs, include fluorescein/tetramethylrhodamine, IAEDANS/fluororescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, TEXAS RED/DABCYL, CY5/BH1, CY5/BH2, CY3/BH1, CY3/BH2 and fluorescein/QSY7 dye. BODIPY and TEXAS RED are trademarks of Molecular Probes, Inc. (Eugene, OR), covering chemical fluorescent dyes. CY, CY3, and CY5 are trademarks of GE Healthcare UK Limited, covering chemical fluorescent dyes. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY 7 dyes advantageously eliminate the potential problem of background fluorescence resulting from direct (i.e., non-sensitized) acceptor excitation. QSY is a trademark of Molecular Probes, Inc. (Eugene, OR), covering fluorescence-quenching dyes. Preferred fluorophore moieties that can be used as one member of a donor-acceptor pair include fluorescein, ROX, and the CY dyes (such as CY5). ROX is a trademark of Thermo Fisher Scientific, Inc., covering a chemical fluorescent dye. Highly preferred quencher moieties that can be used as another member of a donor-acceptor pair include DABCYL and the BLACK HOLE QUENCHER moieties which are available from Biosearch Technologies, Inc., (Novato, CA). BLACK HOLE QUENCHER is a trademark of Biosearch Technologies, Inc. (Petaluma, CA) covering chemical dyes for fluorescent energy transfer. Synthetic techniques and methods of bonding labels to nucleic acids and detecting labels are well known in the art (e.g., see Sambrook et al., Molecular Cloning, A Laboratory Manual, 2nd ed. (Cold Spring Harbor Laboratory Press, Cold Spring Harbor, NY, 1989), Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. No. 5,283,174; Kourilsky et al., U.S. Pat. No. 4,581,333), and Becker et al., European Patent App. No. 0 747 706.

Chemical Composition of Probes

Probes in accordance with the invention comprise agents able to complex with analytes. Examples of useful probes include protein probes, such as antibody probes, and polynucleotide or nucleic acid probes.

Nucleosides or nucleoside analogs of preferred polynucleotide probes comprise nitrogenous heterocyclic bases, or base analogs, where the nucleosides are linked together, for example by phospohdiester bonds to form a polynucleotide. Accordingly, a probe may comprise conventional ribonucleic acid (RNA) and/or deoxyribonucleic acid (DNA), but also may comprise chemical analogs of these molecules. The "backbone" of a probe may be made up of a variety of linkages known in the art, including one or more sugar-phosphodiester linkages, peptide-nucleic acid bonds (sometimes referred to as "peptide nucleic acids" as described by Hyldig-Nielsen et al., PCT Int'l Pub. No. WO 95/32305), phosphorothioate linkages, methylphosphonate linkages or combinations thereof. Sugar moieties of the probe may be either ribose or deoxyribose, or similar compounds having known substitutions, such as, for example, 2'-O-methyl ribose and 2' halide substitutions (e.g., 2'-F). The nitrogenous bases may be conventional bases (A, G, C, T, U), known analogs thereof (e.g., inosine or "I"; see *The Biochemistry of the Nucleic Acids* 5-36, Adams et al., ed., 11$^{th}$ ed., 1992), known derivatives of purine or pyrimidine bases (e.g., N$^4$-methyl deoxygaunosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines (see, Cook, PCT Int'l Pub. No. WO 93/13121) and "abasic" residues where the backbone includes no nitrogenous base for one or more residues of the polymer (see Arnold et al., U.S. Pat. No. 5,585,481). A probe may comprise only conventional sugars, bases and linkages found in RNA and DNA, or may include both conventional components and substitutions (e.g., conventional bases linked via a methoxy backbone, or a nucleic acid including conventional bases and one or more base analogs).

Preferred Nucleic Acid Amplification Reaction Formats

Preferred nucleic acid amplification methods may employ either thermocycling to alternately denature double-stranded nucleic acids and hybridize primers; or alternatively may employ isothermal reaction mechanisms. The polymerase chain reaction (Mullis et al., U.S. Pat. No. 4,683,195; Mullis, U.S. Pat. No. 4,683,202; and Mullis et al., U.S. Pat. No. 4,800,159), commonly referred to as PCR, uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA (Gelfand et al., "Reverse Transcription with Thermostable DNA Polymerases—High Temperature Reverse Transcription," U.S. Pat. Nos. 5,322,770 and 5,310,652). Another method is strand displacement amplification (Walker, G. et al. (1992), *Proc. Natl. Acad. Sci. USA* 89, 392-396; Walker et al., "Nucleic Acid Target Generation," U.S. Pat. No. 5,270,184; Walker, "Strand Displacement Amplification," U.S. Pat. No. 5,455,166; and Walker et al. (1992) *Nucleic Acids Research* 20, 1691-1696), commonly referred to as SDA, which uses cycles of annealing pairs of primer sequences to opposite strands of a target sequence, primer extension in the presence of a dNTP to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (European Pat. No. 0 684 315). Other amplification methods include: nucleic acid sequence based amplification (Malek et al., U.S. Pat. No. 5,130,238), commonly referred to as NASBA; one that uses an RNA replicase to amplify the probe molecule itself (Lizardi, P. et al. (1988) *BioTechnol.* 6, 1197-1202), commonly referred to as Qβ replicase; a transcription-based amplification method (Kwoh, D. et al. (1989) *Proc. Natl. Acad. Sci. USA* 86, 1173-1177); self-sustained sequence replication (Guatelli, J. et al. (1990) *Proc. Natl. Acad. Sci. USA* 87, 1874-1878; Landgren (1993) *Trends in Genetics* 9, 199-202; and Lee, H. et al., NUCLEIC ACID AMPLIFICATION TECHNOLOGIES (1997)); and, transcription-mediated amplification (Kacian et al., "Nucleic Acid Sequence Amplification Methods," U.S. Pat. No. 5,480,784; and Kacian et al., U.S. Pat. No. 5,399,491), commonly referred to as TMA. For further discussion of known amplification methods see Persing, David H., 1993, "In Vitro Nucleic Acid Amplification Techniques" in Diagnostic Medical Microbiology: Principles and Applications (Persing et al., Eds.), pp. 51-87 (American Society for Microbiology, Washington, DC). Other illustrative amplification methods suitable for use in accordance with the present invention include rolling circle amplification (RCA) (Lizardi, "Rolling Circle Replication Reporter Systems," U.S. Pat. No. 5,854,033); Helicase Dependent Amplification (HDA) (Kong et al., "Helicase Dependent Amplification Nucleic Acids," U.S. Pat. Appln. Pub. No. US 2004-0058378 A1); and Loop-Mediated Isothermal Amplification (LAMP) (Notomi et al., "Process for Synthesizing Nucleic Acid," U.S. Pat. No. 6,410,278).

Preferred transcription-based amplification systems of the present invention include TMA, which employs an RNA polymerase to produce multiple RNA transcripts of a target region (e.g., Kacian et al., U.S. Pat. Nos. 5,480,784 and 5,399,491; and Becker et al., "Single-Primer Nucleic Acid Amplification Methods," U.S. Pat. Appln. Pub. No. US 2006-0046265 A1). Transcription mediated amplification (TMA) uses a "promoter oligonucleotide" or "promoter-primer" that hybridizes to a target nucleic acid in the presence of a reverse transcriptase and an RNA polymerase to form a double-stranded promoter from which the RNA polymerase produces RNA transcripts. These transcripts can become templates for further rounds of TMA in the presence of a second primer capable of hybridizing to the RNA transcripts. Unlike PCR, LCR or other methods that require heat denaturation, TMA is an isothermal method that uses an RNAse H activity to digest the RNA strand of an RNA:DNA hybrid, thereby making the DNA strand available for hybridization with a primer or promoter-primer.

In one illustrative TMA method, one amplification primer is an oligonucleotide promoter-primer that comprises a promoter sequence which becomes functional when double-stranded, located 5' of a target-binding sequence, which is capable of hybridizing to a binding site of a target RNA at a location 3' to the sequence to be amplified. A promoter-primer may be referred to as a "T7-primer" when it is specific for T7 RNA polymerase recognition. Under certain circumstances, the 3' end of a promoter-primer, or a sub-population of such promoter-primers, may be modified to block or reduce primer extension. From an unmodified promoter-primer, reverse transcriptase creates a cDNA copy of the target RNA, while RNAse H activity degrades the target RNA. A second amplification primer then binds to the cDNA. This primer may be referred to as a "non-T7 primer" to distinguish it from a "T7-primer." From this second amplification primer, reverse transcriptase creates another DNA strand, resulting in a double-stranded DNA with a functional promoter at one end. When double-stranded, the promoter sequence is capable of binding an RNA polymerase to begin transcription of the target sequence to which the promoter-primer is hybridized. An RNA polymerase uses this promoter sequence to produce multiple RNA transcripts (i.e., amplicons), generally about 100 to 1,000 copies. Each newly-synthesized amplicon can anneal with the second amplification primer. Reverse transcriptase can then create a DNA copy, while the RNAse H activity degrades the RNA of this RNA:DNA duplex. The promoter-primer can then bind to the newly synthesized DNA, allowing the reverse transcriptase to create a double-stranded DNA, from which the RNA polymerase produces multiple amplicons.

Preferred Analyte Polynucleotides

The present invention is not limited to the use of particular nucleotide sequences, nucleic acid analytes, primers or hybridization probes. Thus, the specific oligonucleotides used in the Examples are not essential features of the present invention.

Preferred analyte polynucleotides include nucleic acids from disease-causing organisms, including viruses, bacteria, fungi and protozoa. Examples of highly preferred analyte polynucleotides from viruses are nucleic acids from the human immunodeficiency viruses (HIV-1 and HIV-2), the hepatitis B virus (HBV), the hepatitis C virus (HCV), human papillomaviruses (HPV), Dengue virus (DEN), Chikungunya virus (CHIKV), etc. Preferred analyte polynucleotides from bacteria, fungi and protozoa that can be quantitated according to the methods disclosed herein include the ribosomal RNAs (rRNA). Examples of bacteria that are highly preferred as sources of analyte polynucleotides include *Chlamydia trachomatis* (Gram-negative cells that are obligate intracellular organisms), members of the genus *Campylobacter* (*C. jejuni*, *C. coli*, *C. laridis*), members of the genus *Enterococcus* (*E. avium*, *E. casseliflavus*, *E. durans*, *E. faecalis*, *E. faecium*, *E. gallinarum*, *E. hirae*, *E. mundtii*, *E. pseudoavium*, *E. malodoratus*, and *E. raffinosus*), *Haemophilus influenzae*, *Listeria* momocyto genes, *Neisseria gonorrhoeae*, *Staphylococcus aureus*, Group B Streptococci, *Streptococcus pneumoniae*, *Mycobacterium tuberculosis*, *Mycobacterium avium*, *Mycobacterium intracellulare*, *Mycobacterium gordonae*, *Mycobacterium kansasii*. Examples of fungi that are highly preferred as sources of analyte polynucleotides include: *Blastomyces dermatitidis*, members of the genus *Candida* (*C. albicans*, *C. glabrata*, *C. parapsilosis*, *C. diversus*, *C. tropicalis*, *C. guilliermondii*, *C.*

*dubliniensis*), *Histoplasma capsulatum, Coccidioides immitis*. Examples of protozoa that are highly preferred as sources of analyte polynucleotides include blood and tissue protozoa, such as members of the genus *Plasmodium* (*P. malariae, P. falciparum, P. vivax*), as well as protozoa which infect the gastrointestinal tract such as *Giardia lamblia* and *Cryptosporidium parvum*.

The disclosed method also can be used for detecting nucleic acids that are of human origin, such as mRNAs that are over-expressed or under-expressed in disease states, including cancers. One example of a gene that is present at an increased copy number in breast and ovarian adenocarcinomas is the HER-2/neu oncogene which encodes a tyrosine kinase having certain features in common with the epidermal growth factor receptor (EGFR). U.S. Pat. No. 4,968,603 describes the value of measuring the increased copy number of the HER-2/neu gene, or the HER-2/neu mRNA as a tool for determining neoplastic disease status. Thus, for example, the method described herein can be employed in quantitative nucleic acid amplification protocols whereby the cellular content of HER-2/neu polynucleotides is determined.

Indeed, the method described herein is broadly applicable to numerous nucleic acid targets and is easily extended to procedures for quantifying any given analyte polynucleotide in a test sample.

Apparatus and Transformation Alternatives

An apparatus useful for carrying out the disclosed method typically will include a holder for the sample undergoing testing, an optical detection mechanism that detects and/or quantifies signals indicating the magnitude of probe binding for IC and analyte probes, and a processor (e.g., a computer) that analyzes data and determines whether the analyte is present or absent, or even whether such a determination is possible. A preferred example of such an apparatus is a nucleic acid amplification and detection device. The method implemented on the apparatus may involve hybridization probes, and the detection of optical signals generated by detectable labels may take place at constant temperature (e.g., ambient temperature, or a different constant temperature). In accordance with the invention, it is not a requirement to gather optical signal data at different temperatures in order to determine the presence or absence of analyte in a test sample. A preferred structure that maintains the constant temperature is a temperature-controlled incubator. The temperature-controlled incubator is optional if signal detection takes place at ambient temperature. Of course, the apparatus may also include a temperature-controlled incubator for amplifying nucleic acids, although that incubator need not be used during the step of detecting optical signals used for determining the presence or absence of analyte in a sample. For example, the holder may be contained within the temperature-controlled incubator to maintain its constant temperature, or may be independent of the temperature-controlled incubator which serves in steps related to nucleic acid amplification or some other process. Preferably, the apparatus is configured to hold a multiwell plate or a plurality of tubes. In one embodiment, the optical detection mechanism includes a luminometer that detects light output from chemiluminescent reactions. In a different embodiment, the optical detection mechanism includes a fluorescence detector (i.e, a fluorometer). In the case of nucleic acid analysis, detection of hybridization signals preferably takes place at the conclusion of an amplification reaction, which is sometimes referred to as "end-point detection." This is distinguished from real-time detection, wherein the detection step is performed continuously or periodically as the amplification reaction is taking place. Preferably, the addition of probes specific for IC and analyte nucleic acids (e.g., amplification products) to a nucleic acid amplification reaction mixture is performed by an automated testing instrument. In a generally preferred embodiment, the apparatus that carries out the disclosed method typically will include a computer or processor programmed with software instructions, or be capable of executing software instructions, for determining whether a test reaction is invalid, whether a test result is valid and negative for the presence of analyte (i.e., the sample undergoing testing does not include analyte), or whether a sample undergoing testing is positive for the presence of analyte.

In certain instances, transformation of reagents (e.g., deoxyribonucleotide triphosphates, and/or ribonucleotide triphosphates) into amplicons also is preferred when practicing the present invention. This may involve contacting a template nucleic acid with one or more priming oligonucleotides (e.g., "primers"), and then enzymatically extending the priming oligonucleotides in a template-dependent fashion.

In certain other instances, transformation of reagents may involve transformation of an indicator reagent to a detectable form, where that detectable form indicates the presence of IC or analyte in a starting sample or reaction mixture.

Software

Software products, whether in the form of machine-readable instructions recorded in tangible form (e.g., a machine-readable medium such as a disk having instructions recorded thereon using electronic, magnetic or optical data storage), or loaded into a device that is a component of an apparatus for processing samples and acquiring results (e.g., a nucleic acid amplification device that performs probe hybridization and detection), represent part of the subject matter embraced by the present description. As well, a device for processing samples and acquiring results (e.g., a nucleic acid amplification device that performs probe hybridization and detection) that operates using the software also is embraced by the present description. Of course, the software can be loaded into a general purpose computer linked to the device for processing samples and acquiring results. Alternatively, the software be loaded into a computing device that is an integral component of the device for processing samples and acquiring results.

Calibration Software

The software feature of the invention optionally may include instructions for processing input results from one or more calibration standards. As a result there will be established a validity cutoff and an analyte cutoff, where these cutoffs are useful for determining whether an assay result is valid or invalid, and whether a sample undergoing testing included, or did not include an analyte. More particularly, the software processes results from a negative calibrator (i.e., a calibration standard that does not include any added analyte). Highly preferred software applications regard detection of nucleic acids, using techniques that involve nucleic acid amplification procedures. Of course, a nucleic acid amplification reaction carried out using the negative calibrator will include the internal control, whether as a component of the calibrator or added separately.

Preferred software is capable of establishing threshold cutoffs for determining validity of the assay process, as well as determining the presence or absence of analyte in a sample undergoing testing. The instrument used for performing procedures preferably includes a temperature-controlled incubator in which nucleic acid amplification reactions take place. More preferably, the instrument is further configured for performing nucleic acid hybridization reactions (e.g., at the conclusion of amplification reactions), and detecting probe hybrids. The software is generally capable of receiving quantitative inputs from one or more negative calibrator trials, where each trial includes a reaction (e.g., nucleic acid amplification, and probe hybridization and detection) carried out using IC in the absence of added analyte, and where reaction products of the negative calibrator trials are detected by single channel detection. In this detection format, signals indicating the presence of IC-specific and analyte-specific reaction products are quantified without distinguishing signals specific for either of the two reaction products. The software is further capable of establishing a validity cutoff having a value less than 100% of the magnitude of the combined IC signal plus analyte signal measured for the negative calibrator trial(s). Test reactions (i.e., reactions carried out using test samples) yielding a combined IC plus analyte signal of a magnitude that meets or exceeds the validity cutoff will be judged as valid (i.e., demonstrating that all assay process steps were functional). Test reactions yielding a combined IC plus analyte signal of a magnitude less than the validity cutoff will be judged as invalid. The software is further capable of receiving results from one or more positive calibrator trials, where each trial includes a reaction (e.g., nucleic acid amplification, and probe hybridization and detection) carried out using IC and a predetermined amount of analyte that yields detectable reaction products for both IC and analyte, and where products of the positive calibrator trials are, like the products of the negative calibrator trial(s), detected by single channel detection. The software is further capable of establishing an analyte cutoff having a value greater than 100% of the magnitude of the combined IC plus analyte signal measured for the negative calibrator trial(s), and optionally also a fractional amount less than 100% of the positive calibrator trial. Test samples yielding a combined IC plus analyte signal having a magnitude that meets or exceeds the analyte cutoff will indicate that the sample undergoing testing is includes the analyte. Test samples yielding a combined IC plus analyte signal of a magnitude less than the analyte cutoff will indicate that the sample undergoing testing does not include analyte.

A noteworthy feature of the calibration software component of the present disclosure is the fact that two cutoffs are established, and that these cutoffs are established using quantitative signal data based on a single reading of a combined signal, where the combined signal includes contributions from IC and analyte, but where the combined signal makes no distinction between the origin of the signal contributions. Instead, the software is capable of determining that analyte is present in a test sample by comparing the combined signal against the determined threshold cutoffs.

Analytical Software

Software for analyzing experimental data obtained in connection with the invented technique is able to determine whether the magnitude of a combined IC and analyte signal is above or below a plurality of threshold cutoffs. For example, preferred software instructions specify performance of a step to determine whether the magnitude of the combined signal meets or exceeds a threshold (i.e., the analyte cutoff) for determining the presence of analyte in a reaction mixture. If the combined signal meets or exceeds the analyte cutoff, then the software may output a result indicating that the sample undergoing testing includes the analyte. Conversely, if the magnitude of the combined signal does not meet or exceed the analyte cutoff (i.e., falls below the analyte cutoff), then the software also can instruct comparison of the magnitude of the combined signal with a validity cutoff to determine whether assay results are valid or invalid. Here, a result wherein the magnitude of the combined signal is below the validity cutoff will be interpreted as indicating an invalid assay. This may require that the test is repeated, and the software may indicate the test is invalid. On the other hand, if the magnitude of the combined signal meets or exceeds the validity cutoff, then the software interprets the assay result as being valid. Again, if the magnitude of the combined signal meets or exceeds the validity cutoff, but does not meet or exceed the analyte cutoff, then the software instructs an output result indicating that the sample undergoing testing does not include the analyte. This result will be considered valid, meaning that the conclusion regarding absence of analyte is accurate, and not due to failure of some assay component. The logic of this processing tree is embodied in the look-up table appearing in Table 1.

In addition to the above, preferred software instructions further can accommodate interpretation of results obtained for an IC-validated assay that detects a plurality of analytes. To simplify description of this aspect of the software, the first analyte (i.e., "Analyte-1") and IC, or amplicons arising therefrom, are detected using a "combined first signal" that is a combined IC plus Analyte-1 signal indicating detection of these targets. Similarly, a "second signal" is used for detecting the second analyte (i.e., "Analyte-2"), or amplicons arising therefrom. Optionally, a third analyte (i.e, "Analyte-3") also can be detected by a "combined second signal," where this signal indicates the presence of either Analyte-2 or Analyte-3, without distinguishing one from the other. The software can receive input information for the second signal, and compare the magnitude of the second signal with a threshold cutoff for detection of Analyte-2 (i.e., the "Analyte-2 cutoff"). The Analyte-2 cutoff optionally can be different from a threshold cutoff used for detection of Analyte-1 (i.e., the "Analyte-1 cutoff"), since Analyte-2 typically will be detected using a label that is distinguished from the label used for detecting Analyte-1. Here the software can instruct performance of a step to determine whether the magnitude of the second signal is above or below the Analyte-2 cutoff. If the magnitude of the second signal meets or exceeds the Analyte-2 cutoff, then the software reports that Analyte-2 is present in the sample undergoing testing. If the magnitude of the second signal is below the Analyte-2 cutoff, the result alternatively could mean that the sample undergoing testing did not include Analyte-2, or that the result is invalid due to inhibition of an assay process step. Regardless of whether the second signal is above or below the Analyte-2 cutoff, the software preferably interrogates the magnitude of the combined first signal. Here again, preferred software instructions specify performance of a step to determine whether the magnitude of the combined first signal meets or exceeds the Analyte-1 cutoff. If the combined first signal meets or exceeds the Analyte-1 cutoff, then the software may output a result indicating that the sample undergoing testing includes Analyte-1. Since the Analyte-1 cutoff is higher than the validity cutoff, the Analyte-1 positive result will automatically validate the assay results, meaning that a second signal falling below the Analyte-2 cutoff will be interpreted by the software as validating the Analyte-2 negative result. In this case the software can generate an output indicating that the sample undergoing testing includes Analyte-1, but does not include Analyte-2. If the magnitude of the combined first signal does not meet or exceed the Analyte-1 cutoff (i.e., falls below the Analyte-1 cutoff), then the software also can instruct comparison of the magnitude of the combined first signal with a validity cutoff to determine whether assay results are valid or invalid. Here, a result wherein the magnitude of the combined first signal is below the validity cutoff will be interpreted by the software as indicating the assay results are invalid only if the second signal also falls below the Analyte-2 cutoff. If the magnitude of the combined first signal is below the validity cutoff, and if the magnitude of the second signal meets or exceeds the Analyte-2 cutoff, then the software reports that the sample undergoing testing includes Analyte-2, but does not include Analyte-1. In this case the second signal can serve to validate assay results, even when the first signal is below the validity cutoff. Likewise, if the combined first signal meets or exceeds the validity cutoff, but falls below the Analyte-1 cutoff, that result will validate the assay results, meaning that the sample undergoing testing does not include Analyte-1. Whether the sample includes Analyte-2 will depend on whether the magnitude of second signal meets or exceeds the Analyte-2 cutoff (in which case the sample includes Analyte-2), or whether the magnitude of the second signal falls below the Analyte-2 cutoff (in which case the sample does not include Analyte-2). The logic of this processing tree is embodied in the look-up table appearing in Table 2.

Illustrative Examples

Following there is an exemplary case where an IC polynucleotide and optionally also distinct first and/or second analyte polynucleotides (i.e., termed, "Analyte-1" and "Analyte-2") were amplified and detected. More specifically, at the conclusion of the amplification reaction the IC amplicon, Analyte-1 amplicon, and Analyte-2 amplicon, if present, were all detected using target-specific hybridization probes. Probes specific for IC and Analyte-1 were labeled with the same chemical species of chemiluminescent label (i.e., an AE label). The probe specific for Analyte-2 amplicons was labeled with a second AE label that was distinguishable from the label used for detecting IC amplicons and Analyte-1 amplicons. The magnitude of the combined probe hybridization signal for IC and Analyte-1 amplicon was measured and compared against two threshold cutoffs to determine assay validity, and the presence or absence of Analyte-1 nucleic acids in the reaction. In accordance with the invention, a combined signal meeting or exceeding the lower of these thresholds (i.e., the validity cutoff) indicates that amplification and detection took place, thereby validating the assay (i.e., "assay valid"). Conversely, a combined signal lower than the validity cutoff indicates the procedure failed, and the assay result is declared "invalid." A combined signal meeting or exceeding a second threshold (i.e., the Analyte-1 cutoff), where the second threshold is higher than the first threshold, indicates that Analyte-1 was present in the sample undergoing testing (i.e., Analyte-1 positive). A combined signal that exceeds the validity cutoff but not the Analyte-1 cutoff indicates the sample is negative for Analyte-1, and that the assay result is valid (i.e., assay valid; Analyte-1 negative). Analyte-2 was detected independently by comparing the hybridization signal for Analyte-2 specific probe against a threshold cutoff specific for that target (i.e., the Analyte-2 cutoff). A signal arising from the Analyte-2 specific probe meeting or exceeding the Analyte-2 cutoff indicates that Analyte-2 was present in the sample undergoing testing. Notably, any sample that was positive for Analyte-2 was considered valid, regardless of the signal detected for IC plus Analyte-1 amplicons. Finally, detection of a combined hybridization signal for IC and Analyte-1 meeting or exceeding the Analyte-1 cutoff, together with a signal arising from the Analyte-2 specific probe meeting or exceeding the Analyte-2 cutoff indicates that the sample undergoing testing included both Analyte-1 and Analyte-2.

Methods employing the acridinium ester labels described below are known in the art of nucleic acid labeling. Indeed, Nelson et al., in U.S. Pat. No. 5,658,737 described simultaneously detecting multiple specific nucleic acid sequences using hybridization probes harboring kinetically distinguishable chemiluminescent labels. Nelson et al., specifically employed different labels to distinguish hybridization of different target-specific probes. Linnen et al., in published U.S. Pat. Appl. No. 2004/0029111 described the use of hybridization probe cocktails for detecting amplified viral nucleic acid targets, and in some cases internal control amplicons. Here the kinetically distinguishable labels were used for discriminating internal control amplicons from analyte amplicons. Trials wherein collections of probes were used for detecting viral amplicons were judged as positive or negative using a single threshold cutoff. The IC-validated assays disclosed by Linnen et al., always required one label for detecting IC amplicons, and a different label for detecting analyte amplicons. As will be apparent from the following description, the disclosed technique includes a new arrangement of detectable labels on probes (e.g., nucleic acid probes) in a single reaction mixture, where that arrangement would have delivered ambiguous results using methods previously disclosed by others.

Example 1 describes an IC-validated assay capable of detecting a first analyte nucleic acid using a single read channel, and only a single species of detectable label. The described assay is further capable of detecting a second analyte using a second species of detectable label, where the second label species is distinguishable from the first label species. In this instance, the IC (i.e., a sequence essentially identical to Analyte-1 except for a scrambled internal probe-binding sequence) and Analyte-1 templates both amplified using a shared pair of primers, thereby defining a competitive IC amplification (i.e., Analyte-1 and IC being amplified by shared primers). However, a non-competitive IC system (i.e., Analyte-1 and IC nucleic acids being amplified by unrelated primers) can be substituted, and falls within the scope of the present method and apparatus. Notably, the assay used in this illustration exhibited 95% positive detection of Analyte-1 and Analyte-2 when the respective targets were present at 30 copies/reaction.

Example 1

IC-Validated Assay for Detecting Two Different Analyte Polynucleotides Using Single Channel Read of Analyte and Process Control Signals In vitro synthesized transcripts served as templates for amplification in conventional TMA reactions. Negative control samples were represented by 400 µl volumes of specimen transport medium (STM) containing no added Analyte-1 or Analyte-2 nucleic acid. Test samples were represented by 400 µl volumes of STM containing either 100 copies of an in vitro transcript for Analyte-1, 100 copies of an in vitro transcript for Analyte-2, or the combination of $10^7$ copies of the Analyte-1 in vitro transcript and $10^4$ copies of the Analyte-2 in vitro transcript. STM is a phosphate-buffered detergent solution which, in addition to lysing cells, protects released RNAs by inhibiting the activity of RNases that may be present in the test sample. Aliquots (100 µl) of target-capture reagent (TCR) containing 200 copies of in vitro synthesized IC transcripts were added to each sample, and mixed gently. This ensured that each reaction received the IC template nucleic acid. The TCR included magnetic particles (Seradyn, Inc.; Indianapolis, Ind.) displaying surface oligo(dT)$_{14}$; and a target-capture oligonucleotide having a stretch of poly(dA) joined to a sequence complementary to either the IC and Analyte-1 nucleic acids, or to the Analyte-2 nucleic acid. Capture reaction mixtures were incubated sequentially at 62° C. for 30 minutes, and room temperature for 30 minutes to allow formation of hybridization complexes made up of target:capture oligomer:immobilized probe on the solid support particles. Hybridization complexes on the particles were separated from other sample components by applying magnetic force to the outside of the vessel, aspirating away other sample components that were not immobilized to the particles, and washing the hybridization complexes on the particles using standard laboratory procedures. Notably, the IC and Analyte-1 transcripts had identical sequences except for a scrambled region between primer binding sites. These native and scrambled sequences served as probe binding sites during the hybridization and detection procedure carried out at the conclusion of the amplification step. Analyte-2 transcripts had sequences that amplified using an independent primer set, where amplification products were not detected by probes used for detecting either IC or Analyte-1.

Amplification reactions were prepared by combining the purified magnetic bead complexes from individual tubes with 75 µl aliquots of an amplification reagent and 200 µl of an inert oil overlay to control evaporation. The TMA reactions were carried out essentially as described by Kacian et al., in U.S. Pat. No. 5,399,491. The disclosure of this U.S. patent is incorporated by reference. The amplification reagent included a pH-buffered mixture of salts, cofactors, deoxyribonucleotide triphosphates (i.e., four dNTPs), and ribonucleotide triphosphates (i.e., four NTPs). The amplification reagent further included a T7 promoter-primer and a non-T7 primer, where the combination was capable of amplifying both IC and Analyte-1 nucleic acid templates. Also included in the amplification reagent were a T7 promoter-primer and non-T7 primer, where the combination was capable of amplifying Analyte-2 nucleic acid. Contents of the tubes were mixed gently, heated briefly to 62° C., and then equilibrated to 42° C. Next, reaction mixtures were combined with 25 µl aliquots of an enzyme reagent, and then incubated at 42° C. for an additional 60 minutes to permit amplification. The enzyme reagent included Moloney murine leukemia virus ("MMLV") reverse transcriptase and T7 RNA polymerase. Reactions resulted in production of amplified DNA and RNA strands when appropriate template polynucleotides were present.

At the conclusion of the 60 minute incubation period, amplification reaction mixtures were subjected to probe hybridization assays. Oligonucleotide probes were prepared using 2'-methoxy (2'-OMe) nucleotide analogs, and labeled with acridinium ester according to procedures that will be familiar to those having an ordinary level of skill in the art. In this instance, the probe specific for IC amplicons and the probe specific for Analyte-1 amplicons were both labeled with ortho-fluoro AE, which is sometimes referred to as a "flasher" because of its rapid kinetic properties during chemiluminescent emission of light. The probe specific for Analyte-2 amplicons was labeled with 2-methyl AE, which is sometimes referred to as a "glower" because of its persistent light production kinetic properties relative to the flasher. The detectable labels were joined to oligonucleotide structures by internally disposed non-nucleotide linkers according to procedures described in U.S. Pat. Nos. 5,585, 481 and 5,639,604, the disclosures of these patents are incorporated by reference. Hybridization reactions were carried out by combining the 100 µl amplification reaction volumes with 100 µl of a buffered probe reagent that included the three oligonucleotide probes dissolved in a succinate-buffered detergent solution. More specifically, the probe reagent was added to each tube, vortexed, and incubated in a water bath at 62° C. for 15 minutes. Following completion of the probe hybridization step, 250 µl of selection reagent (a borate-buffered solution containing a surfactant) was added to each reaction tube. Tubes were vortexed, and then incubated at 62° C. for 10 minutes. After removal from the 62° C. incubator, the tubes were cooled to 19-27° C. for 10-75 minutes and then placed in a LEADER HC+ luminometer (Gen-Probe Incorporated; San Diego, CA) configured for automatic injection of 0.1% hydrogen peroxide and 1 mM nitric acid; followed by injection of a solution containing 1 N NaOH. The combined IC flasher signal and Analyte-1 flasher signal in each reaction was discriminated from the Analyte-2 glower signal by the differential kinetics of light emission, essentially as described by Nelson et al., in U.S. Pat. No. 5,658,737. The disclosure of this U.S. patent is incorporated by reference. Software receiving inputs from the luminometer differentiated between the flasher and glower signals, and reported results for the chemiluminescent reactions in relative light units (RLU). Again, this procedure permitted assignment of signal contributions due to: (1) the combination of IC plus Analyte-1 hybridization; and (2) Analyte-2 hybridization. There was no distinction between the signal arising from the IC probe and the Analyte-1 probe.

Although only two calibrators (i.e., the below described first and second calibrators) would generally be used for establishing cutoffs in assays intended for detecting a single analyte (e.g., Analyte-1) with IC validation, three calibrators were used for illustrating the technique that additionally permitted detection of the second analyte (Analyte-2). More specifically, calibration reactions were carried out to establish the validity cutoff, the Analyte-1 cutoff, and the Analyte-2 cutoff. The first calibration standard (i.e., "Cal(1)") was a negative calibrator consisting of STM buffer, and did not include added Analyte-1 or Analyte-2 nucleic acid. The second calibration standard (i.e., "Cal(2)") was a positive calibrator that included Analyte-1 transcripts in STM buffer, in an amount that provided 400 copies/reaction. The second calibrator did not include any added Analyte-2 transcripts. The third calibration standard (i.e., "Cal(3)") was a positive calibrator that included Analyte-2 transcripts in STM buffer, in an amount that provided 300 copies/reaction. The third calibrator did not include any added Analyte-1 transcripts. It was established ahead of time using standard laboratory procedures that will be familiar to those having an ordinary level of skill in the art that these input amounts of Analyte-1 and Analyte-2 templates resulted in substantially saturating levels of hybridization signal in the probe hybridization and detection procedures. Trials including the calibration standards were processed using the target capture, amplification, and detection procedures described above. Calibration reactions were performed in replicates of three.

Table 3 summarizes results from calibration reactions used for establishing the validity cutoff, the Analyte-1 cutoff, and the Analyte-2 cutoff. The average flasher signal value determined using the negative calibrator (i.e., Cal(1)) was multiplied by 0.5 to establish a validity cutoff. The Analyte-1 cutoff was established by doubling the average flasher signal value determined using the negative calibrator, and then adding 10% of the average flasher signal value determined using the second calibrator (i.e., Cal(2)). The Analyte-2 cutoff was established by arbitrarily calculating 18% of the average glower signal value determined using the third calibrator (i.e., Cal(3)), and then adding the value of the average glower signal measured for Cal(1).

TABLE 3

Establishing Threshold Cutoffs

| Calibrator ID | Avg. Flasher Signal (RLU) | Avg. Glower Signal (RLU) | Determined Cutoff (RLU value) |
|---|---|---|---|
| Cal(1) | 207,910 | 0 | Validity Cutoff (103,955 flasher RLU) |
| Cal(2) | 2,341,958 | 0 | Analyte-1 Cutoff (650,016 flasher RLU) |
| Cal(3) | 0 | 1,962,929 | Analyte-2 Cutoff (353,327 glower RLU) |

Figure 2:
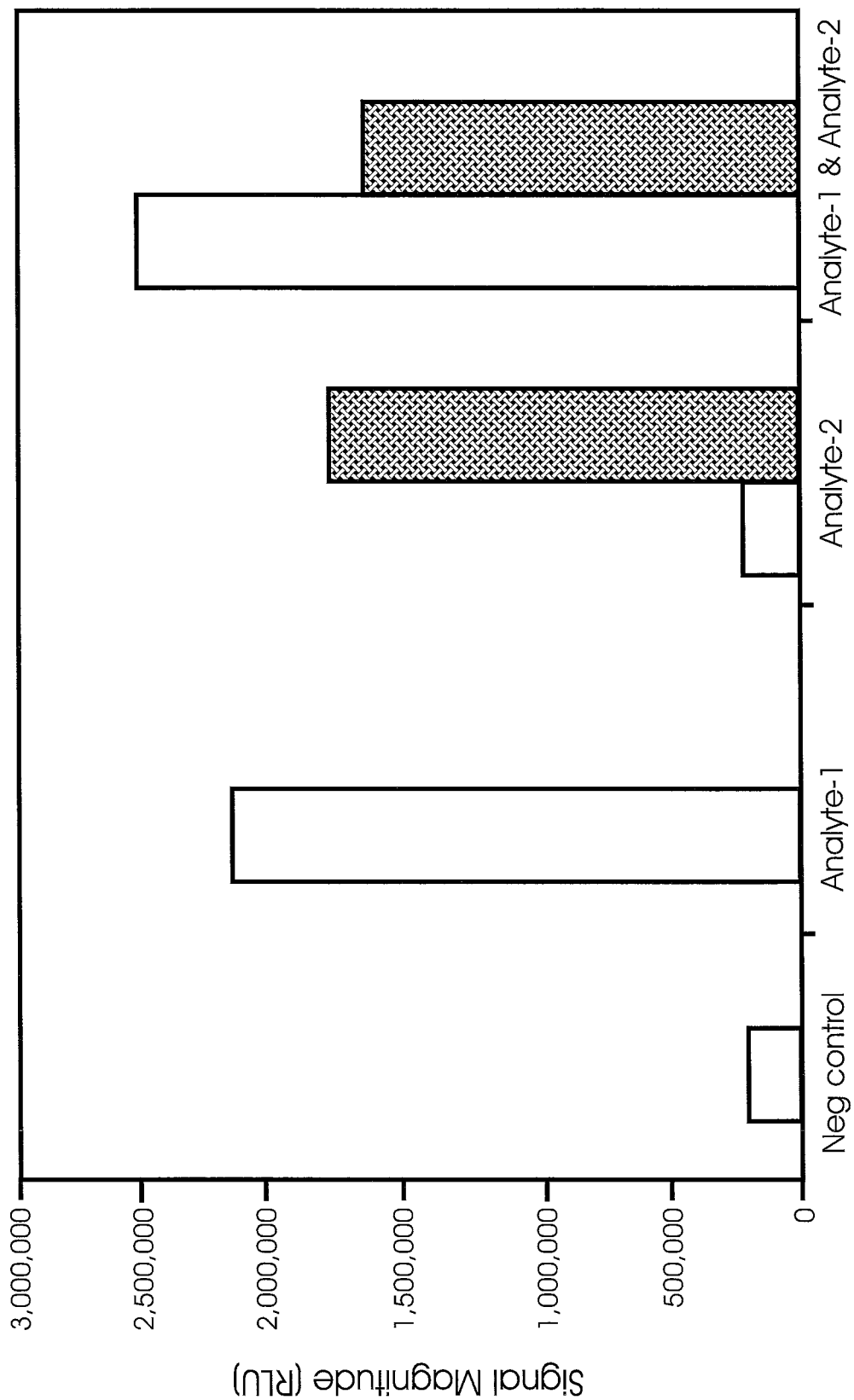
FIG. 2 is a bar graph showing results for a multiplex assay wherein two analytes were detected individually, or in combination. Open bars indicate the magnitude of the combined signal detected using probes specific for IC and Analyte-1. These probes harbored the same type of AE label (i.e., a flasher), and signals represent cumulative probe hybridization signals in the homogenous assay format. All four trials (i.e., Neg control; Analyte-1 only; Analyte-2 only; and Analyte-1 & Analyte-2) gave detectable flasher signals. Filled bars indicate the magnitude of signal detected using a probe specific for Analyte-2, where that probe harbored a type of AE (i.e., a glower) different from the type used for labeling the probes specific for the IC and Analyte-1. Only trials that included Analyte-2 nucleic acid templates yielded detectable Analyte-2 signals.

Table 4 and FIG. 2 summarize results obtained using the test samples in replicates of ten, and interpreted in view of the threshold cutoffs presented in Table 3. The negative control trials yielded a combined average hybridization signal for the IC plus Analyte-1 flasher probes that exceeded the validity cutoff, thereby establishing that the assay result was valid. However, the magnitude of this signal was below the Analyte-1 cutoff, and so indicated the test sample was negative for the presence of Analyte-1, as expected. Likewise, the Analyte-2 glower signal was below the Analyte-2 cutoff, thereby indicating the test sample was negative for Analyte-2, also as expected. Trials conducted using 100 copies/reaction of the Analyte-1 transcript, and no Analyte-2 transcript, yielded a combined average hybridization signal for the IC plus Analyte-1 flasher probes that exceeded both the validity cutoff and the Analyte-1 cutoff, thereby establishing that the assay result was valid and that the test sample was positive for Analyte-1. These same trials yielded average glower signals below the Analyte-2 cutoff, thereby indicating the test sample was negative for Analyte-2. Trials conducted using 100 copies/reaction of the Analyte-2 transcript, and no Analyte-1 transcript, yielded a combined average hybridization signal for the IC plus Analyte-1 flasher probes that exceeded only the validity cutoff, and not the Analyte-1 cutoff. This indicated the assay results were valid, and established that the test sample was negative for Analyte-1. These same trials yielded average glower signals that exceeded the Analyte-2 cutoff, thereby indicating the test sample was positive for Analyte-2. Finally, trials conducted using $10^7$ copies/reaction of the Analyte-1 transcript, and $10^4$ copies/reaction of the Analyte-2 transcript yielded a combined average hybridization signal for the IC plus Analyte-1 flasher probes that exceeded both the validity cutoff and the Analyte-1 cutoff, thereby establishing that the assay result was valid and that the test sample was positive for Analyte-1. These same trials yielded average glower signals that exceeded the Analyte-2 cutoff, thereby indicating the test sample was also positive for Analyte-2. The conclusions presented in Table 4, based on the results appearing in columns 2 and 3, are consistent with the interpretations set forth above in Table 2. Of course, conclusions presented in Table 4 that are relevant to interpretation of the results obtained using only the IC and Analyte-1 probes (see column 2) are consistent with the interpretations set forth above in Table 1.

TABLE 4

Analysis of Experimental Results

| Trial | Avg. IC plus Analyte-1 flasher signal (RLU) | Avg. Analyte-2 glower signal (RLU) | Conclusion |
|---|---|---|---|
| Negative control | 210,640 | 0 | Assay valid Analyte-1 (−) Analyte-2 (−) |
| Analyte-1 at 100 c/rxn Analyte-2 at 0 c/rxn | 2,090,384 | 0 | Assay valid Analyte-1 (+) Analyte-2 (−) |
| Analyte-1 at 0 c/rxn Analyte-2 at 100 c/rxn | 177,431 | 1,744,838 | Assay valid Analyte-1 (−) Analyte-2 (+) |
| Analyte-1 at $10^7$ c/rxn Analyte-2 at $10^4$ c/rxn | 2,502,884 | 1,620,591 | Assay valid Analyte-1 (+) Analyte-2 (+) |

While the present invention has been described and shown in considerable detail with reference to certain preferred embodiments, those skilled in the art will readily appreciate other embodiments of the present invention. Accordingly, the present invention is deemed to include all modifications and variations encompassed within the spirit and scope of the appended claims.

What is claimed is:

1. A kit for determining the presence or absence of analyte polynucleotides in a sample, the kit comprising:
   an internal control polynucleotide;
   one or more amplification reagents to co-amplify a first analyte polynucleotide and the internal control polynucleotide in a nucleic acid amplification reaction to produce an internal control amplicon, and, if the sample contains the first analyte polynucleotide, a first analyte amplicon; and
   a first hybridization probe having a first label, the first hybridization probe being capable of forming a first detectable hybrid with the first analyte amplicon, but incapable of forming a detectable hybrid with the internal control amplicon,
   a second hybridization probe having a second label, the second hybridization probe being capable of forming a second detectable hybrid with the internal control amplicon, but incapable of forming a detectable hybrid with the first analyte amplicon,
   a negative calibrator comprising the internal control polynucleotide, wherein the negative calibrator does not comprise the first analyte polynucleotide, and
   one or more standards, each standard comprising the internal control polynucleotide and a known amount of the first analyte polynucleotide,
   wherein the first and second labels comprise identical labels.

2. The kit of claim 1, wherein the first and second hybridization probes are packaged in a single container as a combined probe reagent.

3. The kit of claim 2, wherein the amplification reagents to co-amplify the first analyte polynucleotide and the internal control polynucleotide comprise amplification reagents to co-amplify a second analyte polynucleotide in the nucleic acid amplification reaction to produce a second analyte amplicon, wherein amplification reagents to co-amplify the second analyte polynucleotide comprise an independent primer set specific for the second analyte.

4. The kit of claim 2, further comprising
a negative calibrator comprising the internal control polynucleotide, wherein the negative calibrator does not comprise the first analyte polynucleotide, and
one or more standards, each standard comprising the internal control polynucleotide and a known amount of the first analyte polynucleotide.

5. The kit of claim 2, wherein the amplification reagents comprise a reverse transcriptase and deoxyribonucleotide triphosphates.

6. The kit of claim 2, wherein at least one of the first and second hybridization probes comprises a nucleotide analog.

7. The kit of claim 2, wherein at least one of the first and second hybridization probes comprises a backbone with a non-nucleotide linker.

8. The kit of claim 1, wherein the identical labels are either identical fluorescent labels or identical chemiluminescent labels.

9. The kit of claim 1, wherein the amplification reagents to co-amplify the first analyte polynucleotide and the internal control polynucleotide further comprise amplification reagents to co-amplify a second analyte polynucleotide in the nucleic acid amplification reaction to produce a second analyte amplicon, wherein amplification reagents to co-amplify the second analyte polynucleotide comprise an independent primer set specific for the second analyte.

10. The kit of claim 9, further comprising a third hybridization probe having a third label, the third hybridization probe being capable of forming a third detectable hybrid with the second analyte amplicon, but incapable of forming a detectable hybrid with the internal control amplicon or the first analyte amplicon, wherein the third label is distinguishable from the first and second labels.

11. The kit of claim 1, wherein the amplification reagents to co-amplify the first analyte polynucleotide and the internal control polynucleotide further comprise amplification reagents to co-amplify a second analyte polynucleotide in the nucleic acid amplification reaction to produce a second analyte amplicon, wherein amplification reagents to co-amplify the second analyte polynucleotide comprise an independent primer set specific for the second analyte.

12. The kit of claim 11, further comprising a third hybridization probe having a third label, the third hybridization probe being capable of forming a third detectable hybrid with the second analyte amplicon, but incapable of forming a detectable hybrid with the internal control amplicon or the first analyte amplicon, wherein the third label is distinguishable from the first and second labels.

13. The kit of claim 12, further comprising one or more standards comprising the internal control polynucleotide and a known amount of the second analyte polynucleotide.

14. The kit of claim 1, wherein the internal control polynucleotide comprises an RNA transcript.

15. The kit of claim 1, wherein the amplification reagents comprise a reverse transcriptase and deoxyribonucleotide triphosphates.

16. The kit of claim 15, wherein the internal control polynucleotide comprises an RNA transcript.

17. The kit of claim 15, wherein the amplification reagents further comprise ribonucleotide triphosphates, at least one promoter-primer, and an RNA polymerase.

18. The kit of claim 1, wherein at least one of the first and second hybridization probes comprises a nucleotide analog.

19. The kit of claim 18, wherein the amplification reagents comprise a reverse transcriptase, deoxyribonucleotide triphosphates, ribonucleotide triphosphates, at least one promoter-primer, and an RNA polymerase.

20. The kit of claim 1, wherein at least one of the first and second hybridization probes comprises a backbone with a non-nucleotide linker.

21. The kit of claim 20, further comprising
a negative calibrator comprising the internal control polynucleotide, wherein the negative calibrator does not comprise the first analyte polynucleotide, and
one or more standards, each standard comprising the internal control polynucleotide and a known amount of the first analyte polynucleotide.

22. The kit of claim 20, wherein the internal control polynucleotide comprises an RNA transcript.

* * * * *